United States Patent [19]

Maruhashi et al.

[11] Patent Number: 5,403,735
[45] Date of Patent: Apr. 4, 1995

[54] METHOD AND APPARATUS FOR INVESTIGATING AND CONTROLLING AN OBJECT

[75] Inventors: Fumio Maruhashi, Hitachi, Japan; Nobuko Nishimura, Woodland Hills, Calif.; Ryoichi Haga, Hitachi, Japan; Harumi Matsuzaki, Hitachi, Japan; Ryusei Nakano, Kudamatsu, Japan

[73] Assignee: Hitachi, Ltd., Tokyo, Japan

[21] Appl. No.: 735,625

[22] Filed: Jul. 24, 1991

[30] Foreign Application Priority Data

Jul. 25, 1990 [JP] Japan ................. 2-194940

[51] Int. Cl.$^6$ ............... C12N 5/00; G01N 15/14; C12M 1/34; F23N 5/08
[52] U.S. Cl. .................. 435/240.1; 435/260; 435/289; 435/808; 435/291
[58] Field of Search .......... 435/240.1, 240.2, 240.45, 435/243, 289, 260, 291, 808

[56] References Cited

U.S. PATENT DOCUMENTS

| | | | |
|---|---|---|---|
| 3,853,711 | 12/1974 | Heden | 435/291 |
| 4,061,914 | 12/1977 | Green | 250/201 |
| 4,118,280 | 10/1978 | Charles et al. | 435/291 |
| 4,564,444 | 1/1986 | Hiraoka et al. | 210/96.1 |
| 4,720,463 | 1/1988 | Farber et al. | 435/291 |
| 4,792,519 | 12/1988 | Blackburn et al. | 435/243 |
| 5,151,347 | 9/1992 | Delente et al. | 435/243 |
| 5,162,204 | 11/1992 | Matsuzaki et al. | 435/240.2 |

FOREIGN PATENT DOCUMENTS

| | | |
|---|---|---|
| 0175549 | 3/1986 | European Pat. Off. . |
| 0340783 | 4/1989 | European Pat. Off. . |
| 3139310 | 10/1981 | Germany . |
| 32113141 | 3/1982 | Germany . |
| 3823494 | 8/1985 | Germany . |

OTHER PUBLICATIONS

*Patent Abstracts of Japan*, vol. 12, No. 82, Mar. 15, 1988 & JP-A-62 215 383, Sep. 22, 1987 (abstract).
*Patent Abstracts of Japan*, vol. 10, No. 188, (P-473) Jul. 3, 1986 & JP-A-61 032 182 (Hitachi) Feb. 14, 1986 (abstract).
*IEEE Transactions on Energy Conversion*, "A Combustion Diagnosis Method for Pulverized Coal Boilers Using Flame-Image Recognition Technology", vol. EC-1, No. 2, Jun. 1986, New York, U.S., by N. Kurihara, et al.

*Primary Examiner*—Thomas Wyse
*Attorney, Agent, or Firm*—Antonelli, Terry, Stout & Kraus

[57] ABSTRACT

In order to investigate an object, such as a culture of micro-organisms, the object is repeatedly captured at two different magnifications by a suitable image pick-up device. The images at the two different magnifications are then analysed by a suitable picture image recognition device and the results of the repeated analysis are compared, thereby to derive a measurement of the change in the object with time. Thus, for a culture of micro-organisms, the number of cells can be determined at one magnification and the number of microscopic spherical bodies can be determined at another magnification, to obtain a measure of the activity of the culture. Preferably, one or more conditions of the object are then controlled on the basis of the measurement of change.

6 Claims, 20 Drawing Sheets

METHOD AND APPARATUS FOR INVESTIGATING AND CONTROLLING AN OBJECT

BACKGROUND OF THE INVENTION

Field of the Invention

The present invention relates to a method and apparatus for investigating an object, and to a method and apparatus for controlling a condition of that object on the basis of the investigation. It is particularly, but not exclusively, concerned with the situation where that object is a culture of microorganisms.

Summary of the Prior Art

Culture systems based on living micro-organisms are widely used for:

(1) systems for the production of useful substances by culturing animal and/or plant cells, micro-organisms or yeast, for applications of those substances in the fields of medicine, diagnosis and foods, (2) systems of cell activation, e.g. for immunization therapy in the field of medical care, (3) systems for removing hazardous matter by using micro-organisms, for applications in the field of waste water treatment and (4) systems for farming of fish and shellfish in the field of fisheries.

Research for further improving the practical use of such culture systems is proceeding, and it is desirable to improve the efficiency of all of these systems specifically, for the systems (1) and (4) improvement of productivity is desirable, for system (2) improvement of activation efficiency is desirable; and for system (3) improvement of operation stability is desirable.

In system (1), the amount of useful substances produced by cells is extremely small, for example, a few $ng/10^6$ to a few $\mu g/10^6$ cells per day. Therefore to obtain these useful substances on an industrial basis, improvement of cell concentration in the culture liquid, increase in the capacity of the culture tank and activation of cells (improvement of substance production ability of every cell) are desirable. To improve the cell concentration, by accelerating the multiplication of cells and suppressing death of the cells, it is necessary to collect detailed information about the concentration of the cells. For example, the ratio of the number of living cells (viability) to the total number of cells is desirable, as is the ratio of the number of cells having a potential for division (divisible cell ratio) to the number of living cells. For the activation of the cells, the ratio of the number of cells having a high secretion activity (secreting cell ratio) to the number of living cells is needed.

Conventionally, these ratios were obtained by staining dead cells with a staining agent to distinguish the dead cells from living cells and thereafter a magnified image was observed with a microscope as disclosed in JP-A-2-27977 (1990).

Currently, the majority of activity diagnosis methods which make use of the number of cells as an index are performed by human eyes. However, a few known methods make use of picture image processing and count cultured cells.

JP-A-62-201332 (1987) and JP-A-64-029765 (1989) disclosed a method in which living cells (unstained) and dead cells (stained) were recognized separately by making use of a linear spatial filter. Also, JP-A-2-27977 (1990) referred to above disclosed a method in which living cells and dead cells were discriminated by their sizes by making use of a linear spatial filter without injecting a staining agent into the culture liquid for the micro-organisms. However, both these known methods only obtained viability information. In a system for producing useful substances, information concerning the ratio of secreting cells is particularly important. Also, in system (2) mentioned above, information concerning the ratio of divisible cells, which represents an index indicating the ratio of active cells, is important. However no method of obtaining this information under physiological conditions of cells has been proposed.

In an activated sludge processing system (system (3), it is necessary to prevent the phenomenon of bulking, in which no active sludge is sedimented, in order to obtain stable operation, for the prevention thereof, microorganism phase appearing in activated sludge groups is an important information and currently the sedimentation of activated sludge is evaluated on the basis of the ratio between aggregative micro-organisms and filamentous microorganisms.

JP-A-61-21786 (1986) disclosed image picking-up with different magnifications when observing microorganisms in sewage water. However no picture image processing was disclosed.

JP-A-61-32182 (1986) disclosed a method in which images of cell specimens are obtained up with different magnifications and the cells were identified based upon the respective picture image information. In the method disclosed, only cells with no multiplication ability such as blood corpuscles, were considered, i.e. this method only considers objects which do not change substantially during the observation period. This document did describe picture image processing of the picture images.

JP-A-64-53157 (1989) disclosed a method in which skin cell samples are observed by a microscope with one magnification. Then, those samples were observed by the microscope with a higher magnification after storing the current position and the characteristics of the cells were measured via picture image processing.

SUMMARY OF THE INVENTION

As was mentioned above, the majority of systems currently used distinguished between living cells and dead cells, by staining the dead cells with a suitable staining agent. Subsequently, magnified images were observed by a human observer, to obtain a measurement of the viability of the sample. However, such a known system has a number of problems.

(1) In general, a living body culture is a pure culture so that the culture system is isolated from the outside and it is necessary to prevent the introduction of living bodies other than those of the bodies to be cultured. When specimens are taken from a culture liquid and a staining agent is injected, the closed system of the sterile culture system has to be temporarily opened, causing contact with the outside of the system. Therefore various germs may be introduced so that continuation of satisfactory culturing may be disturbed.

(2) Since the culture liquid to which the staining agent has been injected cannot be returned to the culture tank, some culture liquid is lost every time when specimens are taken so that any increase in the frequency of measurement of cell activity diagnosis is limited.

(3) When the cells are caused to multiply in a transparent culture flask, although images of the cells can be observed by placing the flask on a microscope while the flask contains the liquid, a sampling sequence has to be included for injection of the staining agent.

(4) It is difficult to judge whether the stained cells are living cells or dead cells even when such judgment is performed by a human or by recognition via a picture image processing.

(5) No information about the ratio of cells capable of dividing is obtained.

(6) No information about the ratio of cells capable of secreting is obtained.

(7) Accordingly, it is difficult to increase the efficiency of the system.

These problems usually arise even when the living bodies are micro-organisms and yeasts (including micro-organisms and yeasts produced by recombinant technology) and occur independent of whether the activity diagnosis is performed by eye or by a picture image processing. The method of judging whether cells are alive or dead, depending on the size distribution of the cultured cells via a picture image processing as disclosed in JP-A-2-27977 (1990), may at least partially ameliorate problems (1)–(4) but cannot solve problems (5)–(7).

Therefore, the present invention proposes that the optical investigations of an object at two different magnifications are performed repeatedly, and then the variation of the investigated properties may be determined.

Preferably, the data from each investigation of the variation of the properties is stored for each repetition of the optical investigations at the two different magnifications, and then the data so stored, for a plurality of repetitions of the investigation, may be compared.

In a further development, the result of the investigation of the properties of the object may be used to control the object, by generating a control signal on the basis of that investigation of variations, which control signal controls means for determining at least one condition of the object.

With the present invention, within each repetition of the investigation at two different magnifications, the two measurements at the respectively different magnifications may be made simultaneously or sequentially.

The present invention has a wide range of applications, but a preferred application is in the field of culturing of micro-organisms. As was discussed earlier, a culture of micro-organisms may contain cells corresponding to viable micro-organisms, and smaller particles which have been released from dead or dying micro-organisms. With the present invention, the concentration of cells in the culture of micro-organisms can be determined by counting at one magnification, and the concentration of the smaller particles can be obtained by counting the number thereof at a higher magnification. The ratio of these two concentrations gives a good measure of the viability of the culture of the micro-organisms. Thus, the culture of micro-organisms may be scanned by an image pick-up device, with that scanning preferably occurring in two mutually perpendicular directions. In this way, images of the micro-organisms in the culture may be obtained at two different magnifications.

By obtaining such a viability measurement, it is then possible to control the conditions of the culture of micro-organisms so as to maintain the state of the culture substantially constant, at e.g. a high level of micro-organisms of the type desired. For example, when the culture is still growing, it is desirable to maximize the number of micro-organisms which are capable of dividing (and so increasing the number of micro-organisms), and when a steady state is reached, it is desirable to maximise the number of microorganisms capable of secreting the substance which the culture is intended to produce. In general, it is desirable to keep the ratio of small particles to cells to a value less than 2.

Such control may be achieved in any suitable way, e.g. by controlling the supply and removal of culture material from a culture tank.

The present invention is not limited to the culturing of micro-organisms however. It is also possible to make use of the present system in a sewage plant, in which the micro-organisms in the active sewage are investigated. For example, the present invention may investigate the concentration of microorganisms at one magnitude, and investigate the shape of selected micro-organisms at another magnification.

A further application of the present invention is in the control of a furnace, in which the brightness distribution within the flame is investigated at one magnification and then, at a higher magnification, a part of the flame is investigated to determine optically its temperature.

The present invention relates to both methods and apparatus involving the aspects of the present invention discussed above.

BRIEF DESCRIPTION OF THE DRAWINGS

Embodiments of the invention will now be described in detail, by way of example, with reference to the accompanying drawings, in which.

DETAILED DESCRIPTION

First an example of the present invention will be discussed, considering a culture living bodies such as cells of animals and/or plants, yeasts and microorganisms. These living bodies multiply via division or budding. The culture process generally moves from a logarithmic multiplication period in which the living bodies increase exponentially to a dying period in which the concentration thereof decreases via a multiplication period and a steady state period in which the apparent concentration thereof is substantially constant. In culture systems, the aim is to achieve a condition of high density, by increasing the cell concentration in a short time and thereafter maintaining the steady state period for a long time.

The shapes of the living bodies, specifically the cells of animals and/or plants in the above culture processes, vary. In the logarithmic multiplication period and the multiplication period, almost all the cells are complete spherical bodies. However, when the culture is in the steady state period the spherical bodies distort and in the latter half of the steady state period, cells form polyp shaped projections on their surfaces. Furthermore, small spherical bodies are formed by projections which break off the cells. The relationship between these shapes and the activities of the cells is shown in Table 1.

TABLE 1

| | Multiplication period | Steady period |
|---|---|---|
| Shapes | Sphereical body | . Distorted spherical bodies<br>. Formation of projections<br>. Broken-off projections<br>(small spherical bodies) |
| Activity | Large division | Large secretion activity |

TABLE 1-continued

| | Multiplication period | Steady period |
|---|---|---|
| activity | | |

The size of the cells of animals and/or plants is, in general, ten and a few μm to a few tens of a μm, and the size of the above small spherical bodies is of an order of a few μm.

Figure 2:
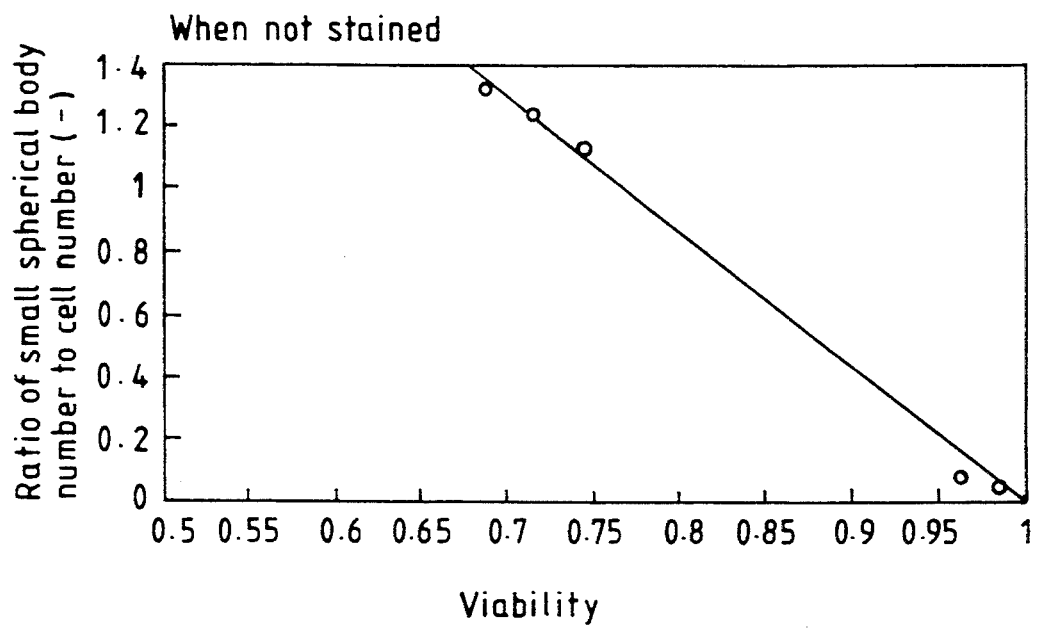
FIG. 2 is a graph showing the relationship existing between the viability and the ratio of the number of small spherical bodies to the number of cells.

FIG. 2 illustrates experimental data showing the relationship between the ratio of the number of small spherical bodies to the total number of cells and the viability of the culture. It can be seen that the two have a linear relationship. Hence, when the ratio of small spherical bodies to cells is determined, the viability of the culture can be obtained. Furthermore, by identifying the different shapes and counting the number of respective shapes, the ratio of secreting cells can be obtained.

Figure 3A:
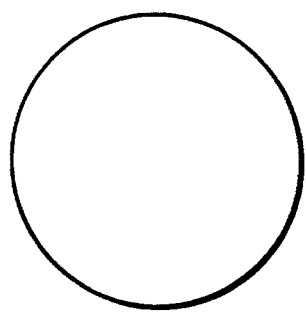
FIGS. 3(a) and 3(b) are schematic diagrams showing examples of cell shapes.

The identification of differences in shapes is performed as follows. When the shape of the cell is a circle as shown in FIG. 3(a), the length of the circumference is expressed as follows, $$\text{radius} \times 2 \times \pi$$

Figure 3B:
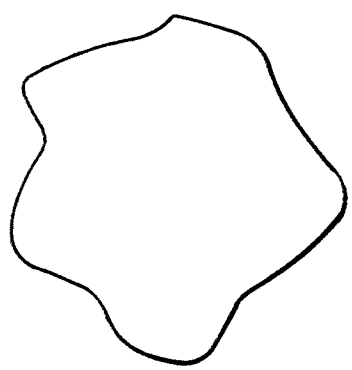

However, when there are recesses and protrusion on the circumference of the cell, as shown in FIG. 3(b), the length of the circumference gradually increases even when the area of two bodies are equal to each other. A value (shape coefficient) obtained by dividing the calculated circumferential length L based upon the radius obtained by the area of the circle, in that, $r = \sqrt{\text{area}/\pi}$, with the actual circumferential length L' as follows, $$\frac{2\sqrt{\text{area}/\pi}}{\text{actual circumferential length}}$$

This can be used as an index indicating how the closeness of the shape of the body to a complete circle (when the body has more recesses and protrusions the value approaches 0 and when the shape is closer to a circle the value approaches 1).

In binary picture images recognizing cells, the more active is the cell, (in other words, the higher the division activity), the more round is its shape. Accordingly, by making use of such a shape coefficient, the differences in shapes may be recognized and an activity diagnosis can be performed.

For such activity diagnosis, the following characteristics are normally required.

(a) Measurement of the total number of cells
(b) Measurement of the number of small spherical bodies
(c) Calculation of the shape coefficient In such an arrangement, the microscopic spherical bodies are highly unlikely to be recognized by processing picture images obtained at a magnification which is appropriate for recognizing the cells. Since picture images of cells in suspension liquid, on many occasions, include stains as their background, a noise removing processing is essential. However, the microscopic spherical bodies are likely ignored as noises, if such noise removing processing is used.

On the other hand, with a magnification which is appropriate to identify microscopic spherical bodies, a single cell may be identified several times in a plurality of picture images. Therefore, when the number of cells are measured by counting, the errors in the counting become significant.

When the cell activity is obtained by use of the shape coefficient, the recesses and protrusions around the circumference have to be recognized accurately. Therefore when a picture image processing device is used in which the resolution (the number of pixels in one screen) is fixed, the magnification of the optical microscope has to be set relatively high.

Thus, according to the present invention the processes (a) and (b) or (c) above have to be performed by changing the magnification of the optical investigation of the bodies.

When the living bodies are yeast, they multiply by budding. Therefore, the relationship between their shapes and their activity is shown in Table 2.

TABLE 2

|  | Multiplication period | Steady period |
| --- | --- | --- |
| Shapes | Protrusion included | . Spherical body<br>. Elliptical body |
| Activity | Large multiplication activity | Large secretion activity |

When there are many cells with protrusions, their multiplication activity is high and when there are many cells of spherical or elliptical shape, their secretion activity is high. This tendency is thus opposite to that of the cells of animals and/or plants explained above. However, differences in shapes are recognized by the shape coefficient. Thus, the divisible cell rate and the secreting cell rate can be obtained. Again, the present invention proposes that the above processes (a) and (c) are performed by changing the magnification of the optical investigation of the bodies.

For activated sludge, when there are many aggregative bacteria, sedimentation is desirable and when there are many filamentous micro-organisms, sedimentation is undesirable. However the sedimentation varies depending upon the types of filamentous micro-organisms and floc shapes which are formed by the aggregative bacteria and the filamentous micro-organisms. Therefore it is necessary to obtain accurate information about the shapes. For this purpose, it is necessary to observe the ratio between the number of aggregative bacteria and the number of filamentous micro-organisms using a low magnification, and to investigate the types of filamentous microorganisms and the floc shapes using a high magnification.

The total number of living bodies is determined by processing the picture images obtained using a low magnification, and the number and type (for filamentous micro-organism) of specific living bodies (such as small spherical bodies, cells with high division activity and cells with high secretion activity) are determined by processing picture images obtained using a high magnification. Based upon these data, information concerning the viability ratio of divisible cells and ratio of secretion cells is obtained to diagnose whether the culture environment is suitable. Based upon the diagnosis result, the culture environment may then be controlled to predetermined conditions, to increase the efficiency of the system.

The conditions of the culture environment which may have to be controlled include factors such as temperature, pH, osmotic pressure, dissolved oxygen concentration, retention time of the liquid, and living body concentration. Among these, temperature, pH, osmotic pressure and dissolved oxygen concentration are respectively controlled in suitable ranges for maintaining a high viability. For controlling the ratio of divisible cells and the ratio of secreting cells the value of (living body concentration)×(retention time of the liquid) is adjusted. When the value of (living body concentration)×(retention time of the liquid) is increased, the ratio of secreting cells can be increased, and when the value (living body concentration)×(retention time of the liquid) is reduced, the ratio of divisible cells can be increased.

In a useful substance production system, the value (living body concentration)×(retention time of the liquid) is set to be low at the initial stage of culture so that a high density of the living bodies can be obtained in a short time. Thereafter, the value of (living body concentration)×(retention time of the liquid) is set to be high to increase the secretion activity of the living bodies and to enhance the productivity of the substance.

In a cell activating system, such as in immunization therapy, the value of (living body concentration)×(retention time of the liquid) is set to be as small as possible to increase the concentration of active living bodies so that it is as high as possible.

In an activated sludge process, the value of (living body concentration)×(retention time of the liquid) is set to be large to decrease the ratio of divisible cells, to suppress any unnecessary increase in the concentration of the living bodies and to decrease excessive sludge, and as well to suppress multiplication of the filamentous micro-organism, to decrease the ratio of the filamentous micro-organism and to increase sedimentation.

Embodiments of the present invention will now be explained with reference to the drawings.

Figure 4:
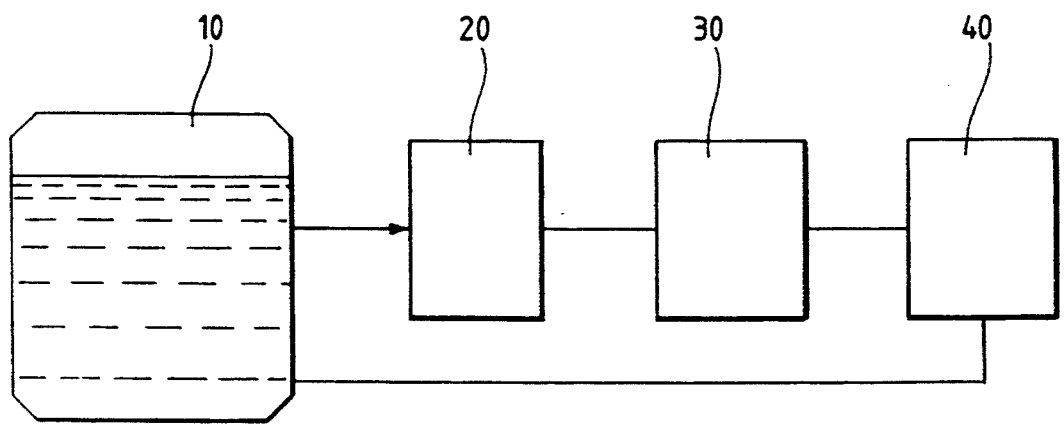
FIG. 4 is a block diagram showing an example of a picture image recognition control system according to one embodiment of the present invention.

FIG. 4 shows an example of a picture image recognition control system according to one embodiment of the present invention. A tank 10 contains liquid containing living bodies in suspension for which reaction and multiplication be controlled. A part of the liquid is withdrawn from the tank 10 and passed to an image pick-up device 20. This image pick-up device, optically magnifies the image of the liquid at two optically different magnifications and the respective magnified images are picked-up as electrical picture image signals by an image picking-up means such as a television camera.

These picture image signals are input to a picture image processing device 30 and the concentration of living bodies in the liquid is determined by processing the picture images obtained with a first magnification and the concentration of a specific type of living body is determined by processing the picture images obtained with a second magnification respectively.

The resulting concentration data for the living bodies measured by the picture image processing device 30 are input to a control device 40, from which the state of the liquid in the tank 10 may be controlled.

Figure 1:
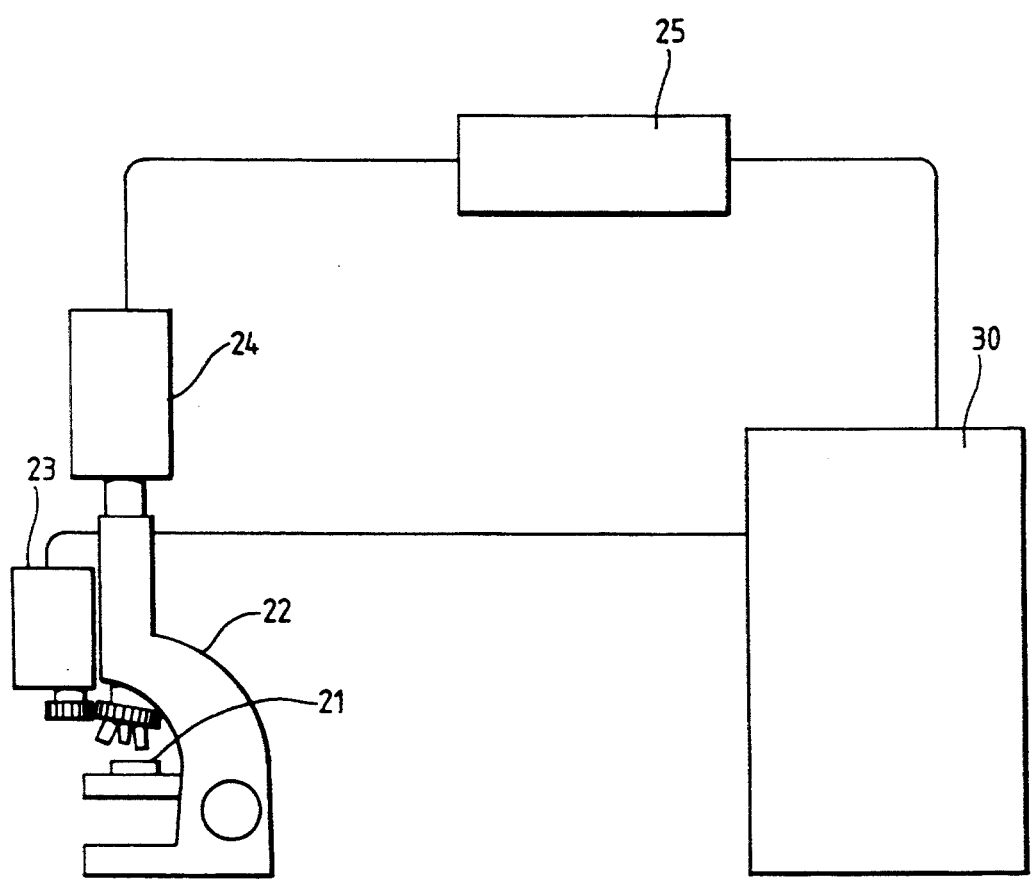
FIG. 1 is a schematic diagram showing an example of an image pick-up device used in the present invention.

FIG. 1 shows in more detail an example of the image pick-up device 20. A transparent container 21 is formed of a transparent material such as glass or plastics, and the object liquid for observation is fed from the liquid tank 10 to the container. In this example, it is preferable to use the technology disclosed in JP-A-2-27977 (1990) so as to allow handling of the observation object while maintaining the physiological conditions of the observation object such as micro-organisms.

An optical microscope 22 magnifies the image of the liquid in the transparent container 21. A television camera 24 converts the magnified image into electrical picture image signals (analog signals). An A/D converter 25 converts the analogue picture image signals from the television camera into a form of digital signals which can be processed in the picture image processing device 30, which are thereafter input to the picture image processing device 30. An automatic objective lens exchange mechanism 23 changes the objective lens used by the optical microscope 22 in response to drive signals from the picture image processing device and varies the magnification of the image of the liquid.

Figure 5:
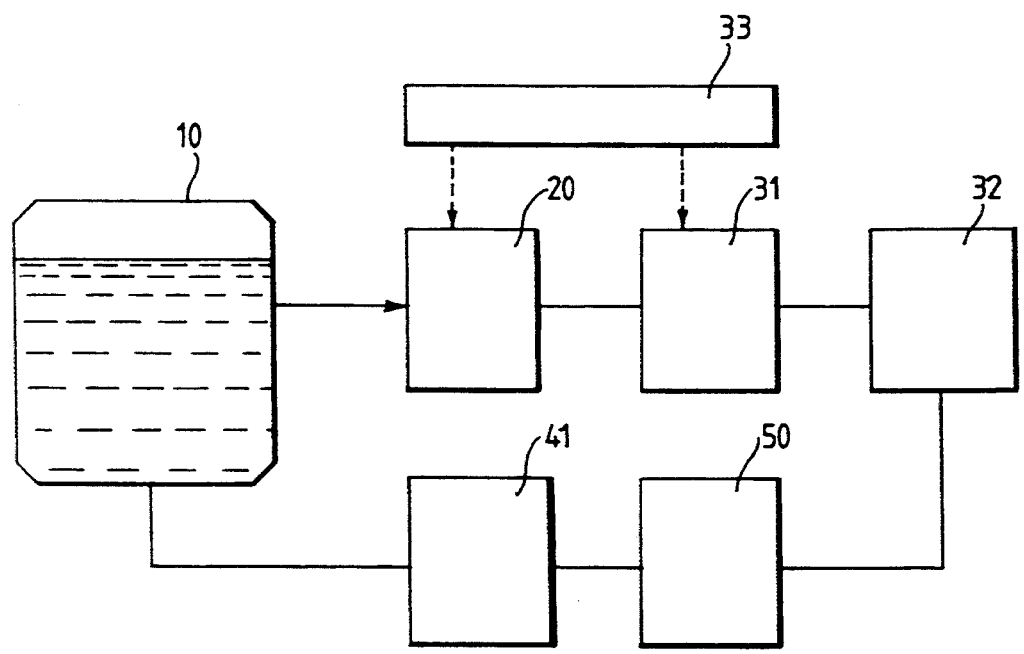
FIG. 5 is a block diagram showing an example of a cell culturing system according to a second embodiment of the present invention.

FIG. 5 shows another embodiment of the present invention. In this embodiment, components corresponding to components of the embodiment of FIG. 4 are indicated by the same reference numerals. In the embodiment of FIG. 5 when the drive signal issues from a timer 33, the liquid containing cells in suspension is sampled and fed to the image pick-up device 20. In this embodiment, the image pick-up device 20 has to have incorporated mechanism therein a such as a pump for supplying the liquid. The image pick-up device 20 magnifies the image of the liquid a plurality of times, with different magnifications, and photographs thereof are generated. The drive signal from the timer is simultaneously transmitted to a picture image recognition device 31 and the photographed images of the liquid are processed without delay and the bodies may then be recognized.

This picture image recognition device 31 generates (recognizes) digital picture images from a plurality of picture images fed to the image pick-up device 20. In such images, cells obtained by processing the picture image obtained at one magnification, and either one of microscopic spherical bodies emitted from cells, as cells emitting microscopic spherical bodies or both, which are obtained by processing the picture images obtained at a different magnification, all take the logical value "1".

A picture image processing device 32 analyzes the binary picture image sent from the picture image recognition device 31, measures the number of living bodies (either of cells, microscopic spherical bodies, cells emitting microscopic spherical bodies) within the screen and calculates their respective concentrations in the liquid. A cell activity diagnosis device 50 calculates the ratio between the two variables, being the concentration of cells and the concentration of microscopic spherical bodies, this ratio, between two variables, being the concentration of cells and the concentration of cells emitting microscopic spherical bodies, or the ratio between three variables, being the concentration of cells, the concentration of microscopic spherical bodies and the concentration of cells emitting microscopic spherical bodies. To obtain these ratios, use is made of the concentration of the living bodies obtained by the picture image processing device 32. Hence, it is possible to diagnose the cell activity in the culture liquid. A culture condition control device 41 controls conditions affecting the state of liquid in a cell culture tank 10 based upon the results of the diagnosis carried out by the cell activity diagnosis device 50.

In the above examples, the drive signals from the timer 33 are transmitted only to the image pick-up device 20 and the picture image recognition device 31. This is because the devices which receive information from the picture image processing device 32 are kept in a waiting condition for picture image signals so that synchronization of processing can be achieved. Of course, it is possible to arrange for all of the devices to be driven by the timer.

Figure 6:
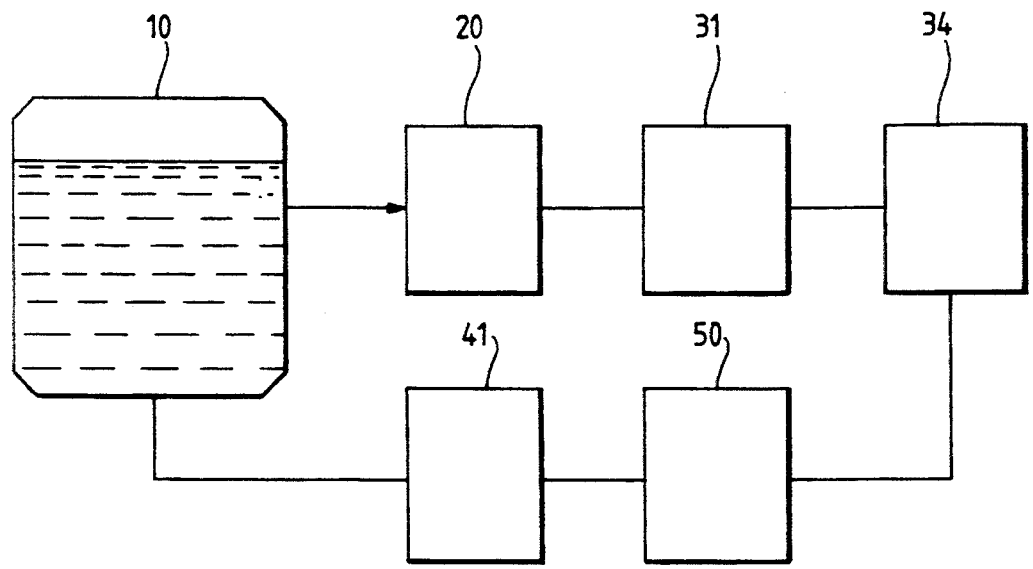
FIG. 6 is a block diagram showing an example of a cell culturing system of a third embodiment of the present invention.

FIG. 6 shows a further embodiment of the present invention. In this embodiment, the picture images of the culture liquid photographed by an image pick-up device 20 are one type and a picture image recognition device 31 recognizes the cells and the microscopic spherical bodies. Thereafter, a statistical value processing device 34 discriminates cells from microscopic spherical bodies based upon the recognized areas of the living bodies, the numbers thereof and calculates the concentrations in the liquid. The functions of the cell activity diagnosis device 50 and the culture condition control device 41 are the same as in the embodiment shown in FIG. 5.

In the above embodiments, the images are picked-up after the liquid is sampled. However another system can be used in which the image pick-up device is located directly in the culture tank and the images of the liquid are picked-up directly from within the tank 10.

Figure 7:
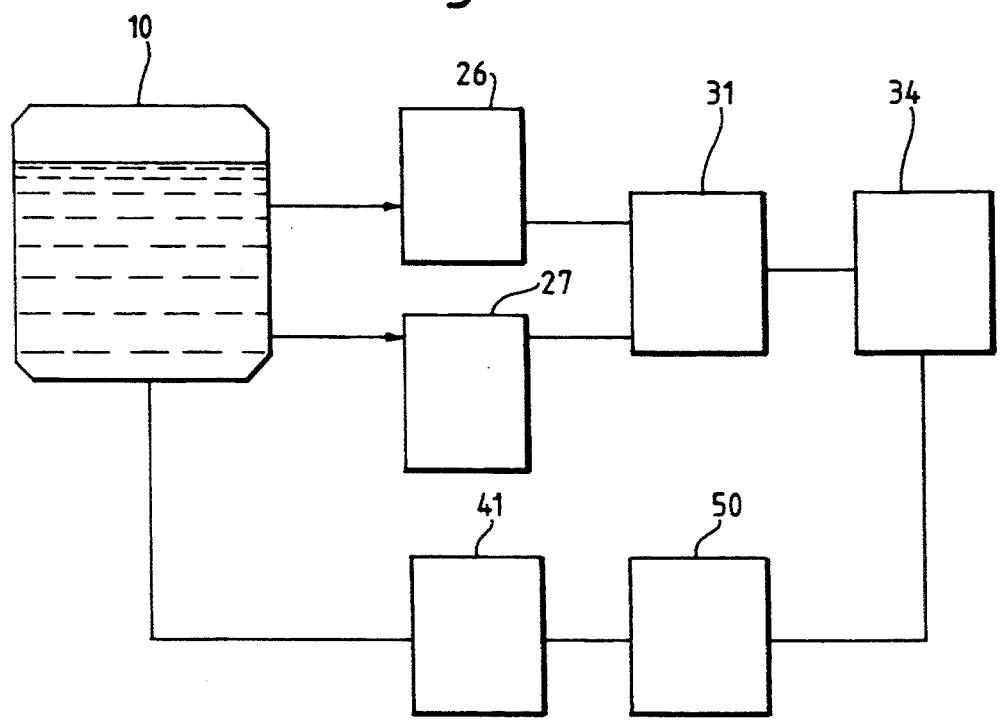
FIG. 7 is a block diagram showing an example of a cell culturing system of a fourth embodiment of the present invention.

FIG. 7 shows a further embodiment of the present invention. The culture liquid sampled from a cell culturing tank is fed to two image pick-up devices 26 and 27. The magnification of the image pick-up device 26 is set at m and the device 26 generates picture images for observing cells. The magnification of the image pick-up device 27 is set at n and the device 27 image generates picture images for observing particles other than cells. The picture images picked-up by the two image pick-up devices 26, 27 are input to a common picture image recognition device 31 with a time displacement therebetween. The device 31 identifies cells from the picture images from the image pick-up device 26 and particles from the picture images from the image pick-up device 27. A statistical value processing device 34 statistically processes the number of cells and particles identified by the picture image recognition device 31 and determines respective concentrations. In this embodiment, the functions of the cell activity diagnosis device 50 and the culture condition control device 41 are the same as in the embodiment shown in FIG. 5.

Figure 8:
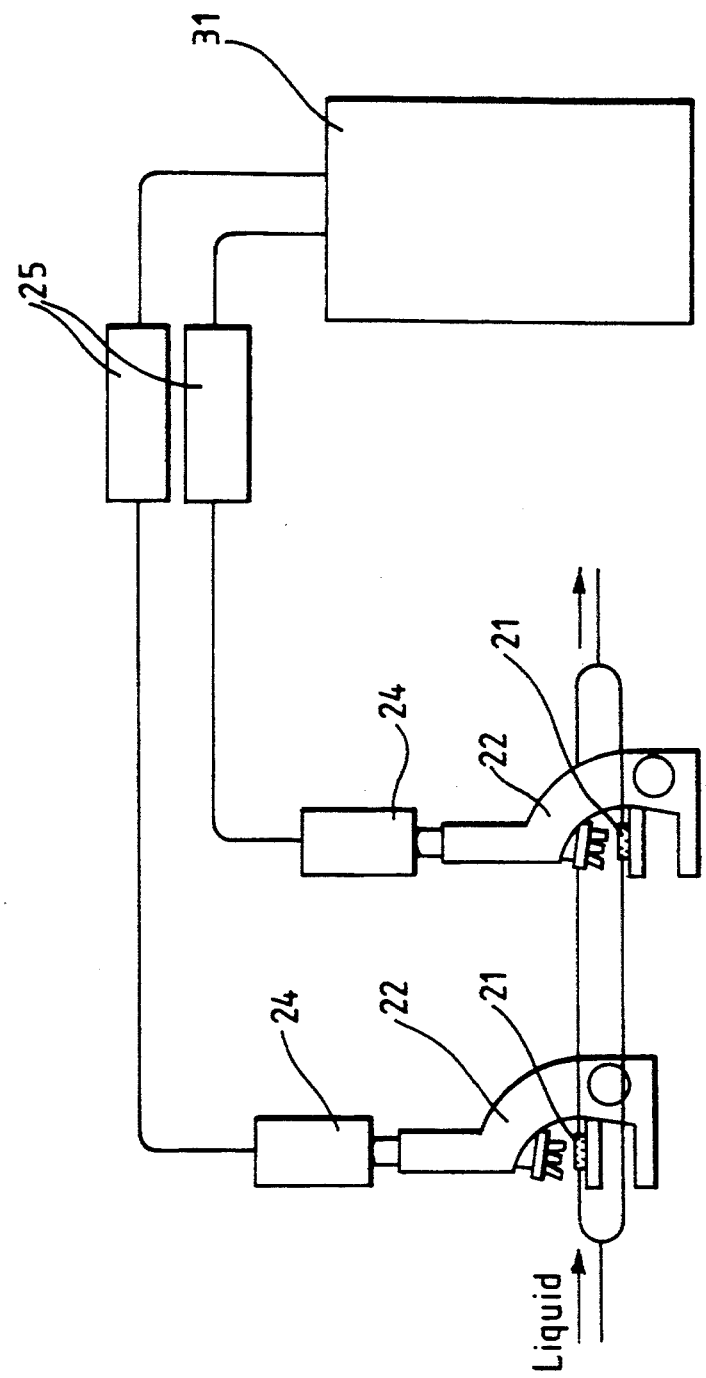
FIG. 8 is a schematic diagram showing an example of a device for forming the two image-pick-up devices shown in FIG. 7.

FIG. 8 shows an example of a device for forming two image pick-up devices. The culture liquid sampled from a cell culturing tank 10 is split into two branches via a tube leading to the image pick-up devices and is fed to two transparent containers. The image is magnified by two optical microscopes 22 by setting the magnification of their objective lenses at m and n respectively and is picked-up by a television camera 24. The respective picture image signals are converted into digital signals via two A/D converters. Thus, use of totally identical two sets of devices, in a hardware sense, is satisfactory.

As shown in FIG. 2, there is a linear relationship between the number of the microscopic particles emitted into the culture liquid and the viability of the cells. Hence an activity determination system can be provided by making use of such relationship. It is necessary to determine parameters for that determination, however a suitable determination means can be prepared based upon prior data. Furthermore, it is also possible to have means for determining the activity by comparing indexes obtained from the judging means prepared by the prior data and from the picked-up images of the present culture liquid.

In another development of the present invention, a system performing measurement of concentrations of cells and microscopic spherical bodies can be formed which is provided with a cell activity diagnosis device in which the development of the activity of the cells is predicted by interpolating the speeds of change of these concentrations at a future time. This interpolating calculation can be achieved by using differential equations.

Figure 19:
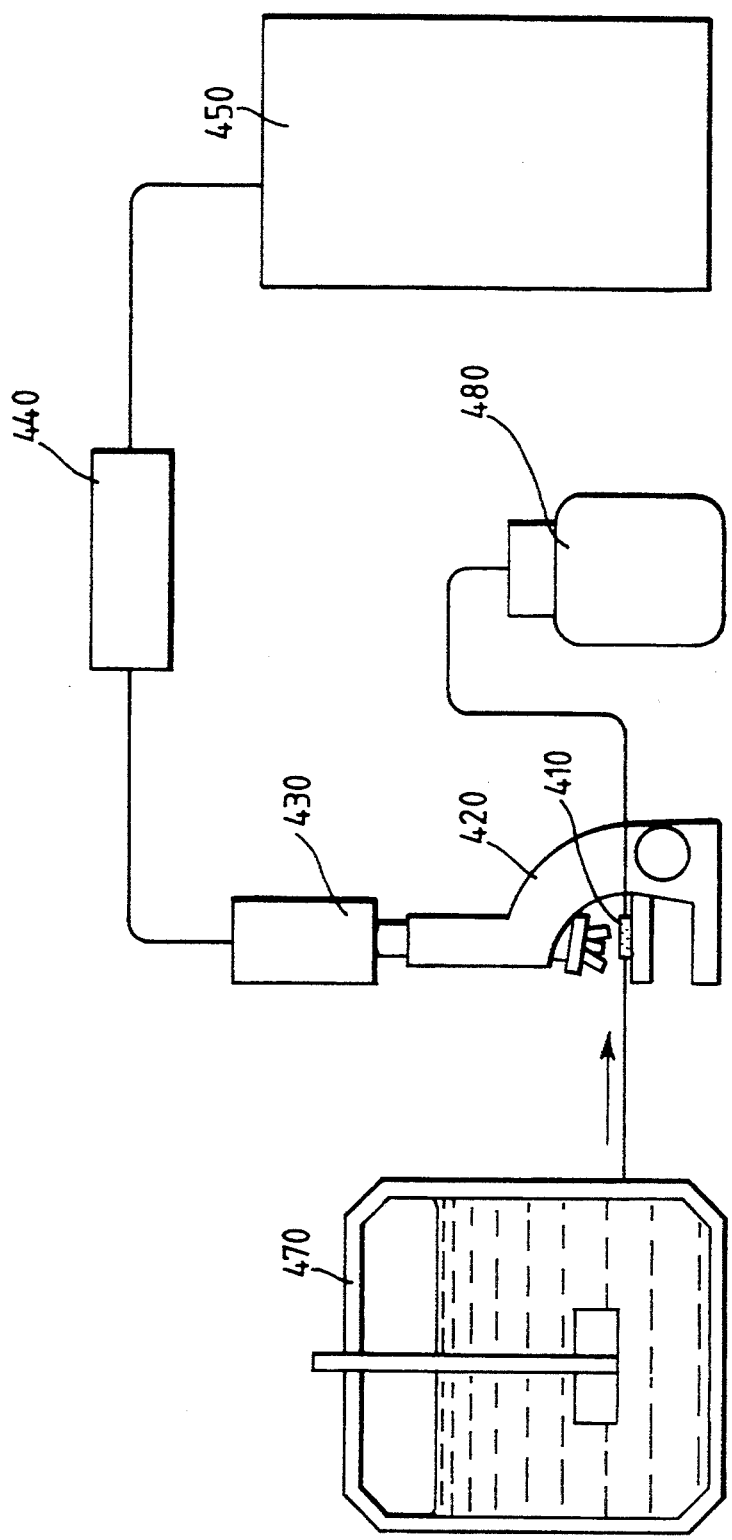
FIG. 19 is a block diagram showing an example of a cell culturing system of a sixth embodiment of the present invention.

Another embodiment of the present invention is illustrated in FIG. 19. In this embodiment, culture liquid is sampled from a cell culturing tank 10 and fed to an image pick-up device 20. The magnified picture images of the culture liquid image picked-up at an image pick-up device 20 are input to a picture image recognition device 31 which identifies cells and microscopic spherical bodies or cells in the course of emitting microscopic spherical bodies or both. A statistical processing device 34 discriminates the cells from the microscopic spherical bodies, determines the member thereof and determines the concentrations of both. A cell activity diagnosis device 50 calculates the activity of the cells in the culture liquid based upon the concentrations of these bodies and generates as output to e.g. a display and printer. Unlike the embodiment shown in FIG. 6, automatic control of the cell culturing tank 10 does not occur. The control depends on the operator who determines the diagnosis results.

Another embodiment may be used which comprises a cell activity diagnosis device, which diagnosing cell activity in the culture liquid by comparing the current activity with prior data in a cell activity judging means.

Figure 20:
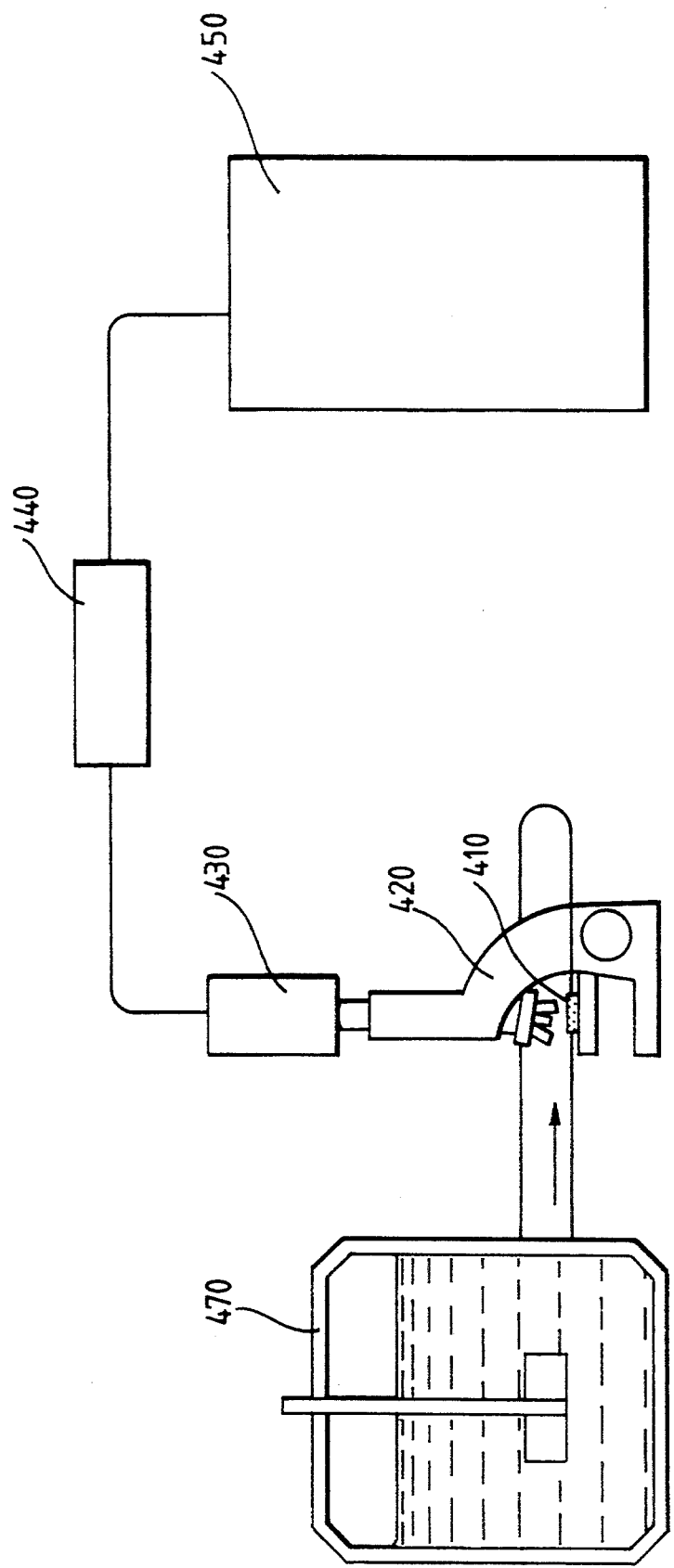
FIG. 20 is a block diagram showing an example of a cell culturing system of a seventh embodiment of the present invention.

Another embodiment will now be discussed with reference to FIG. 20. A timer 33 generates driving signals which drive a pump of an image pick-up device 20. A culture liquid is sampled from a cell culture tank 10 and fed to an image pick-up device 20. Picture images are picked-up a plurality of times with different magnifications and input to a picture image recognition device 31. The cells are recognized from picture images taken at one magnification and the microscopic spherical bodies or the cells in the course of emitting microscopic spherical bodies or both are recognized from picture images taken at another magnification. A picture image processing device 32 analyzes the living bodies (cells, microscopic spherical bodies and cells in the course of emitting microscopic spherical bodies) recognized by the picture image recognition device 31 and determines the respective concentrations. By using the ratios calculated from cells and either one of two kinds of other living bodies or the both as indexes, a cell activity diagnosis device 50 diagnoses the activity of cells in the cell culturing tank 10. The difference between this embodiment and that of FIG. 5 is that in this embodiment the culture condition is not controlled automatically but instead the information about cell activity is passed to the operator.

Figure 9:
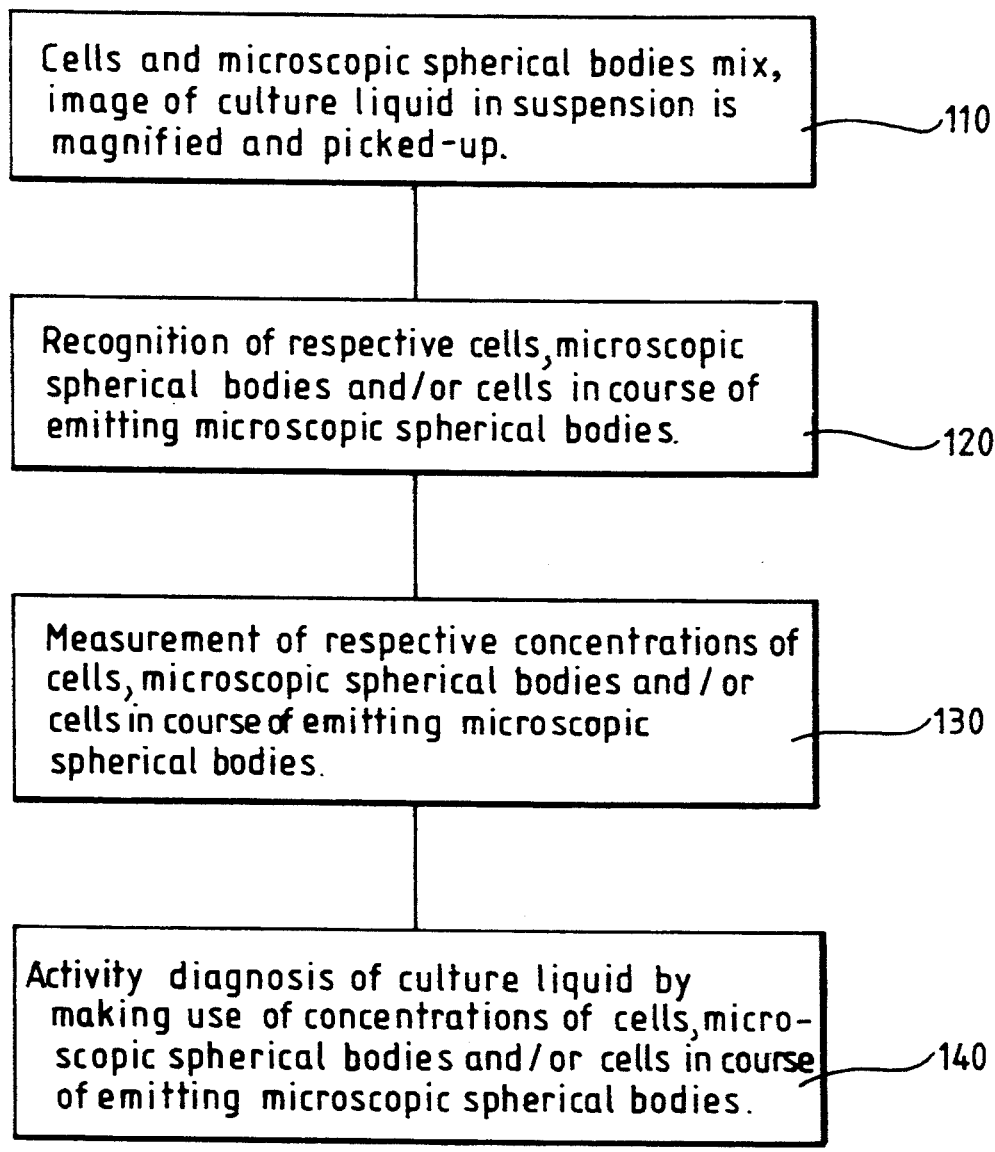
FIG. 9 is a flowchart showing an example of a processing method, making use of a cell activity diagnosis method, according to a fifth embodiment of the present invention.

FIG. 9 shows another embodiment using a cell activity diagnosis method. In step 110, images of culture liquid in which cells and microscopic spherical bodies are mixed in suspension are magnified and their images are picked-up. In step 120, bodies being either microscopic spherical bodies or cells in the course of emitting microscopic spherical bodies or both in the picture images picked-up at the step 110 are recognized by making use of brightness patterns around the living bodies in the picture images. In step 130, the concentrations of the cells and microscopic spherical bodies recognized in step 120 are measured for each kind of living bodies. In step 140, by using ratios calculated from the concentration of cells, the concentration of either microscopic spherical bodies or cells in the course of emitting microscopic spherical bodies or both, the activity of the cells in the culture liquid may be diagnosed.

Figure 10A:
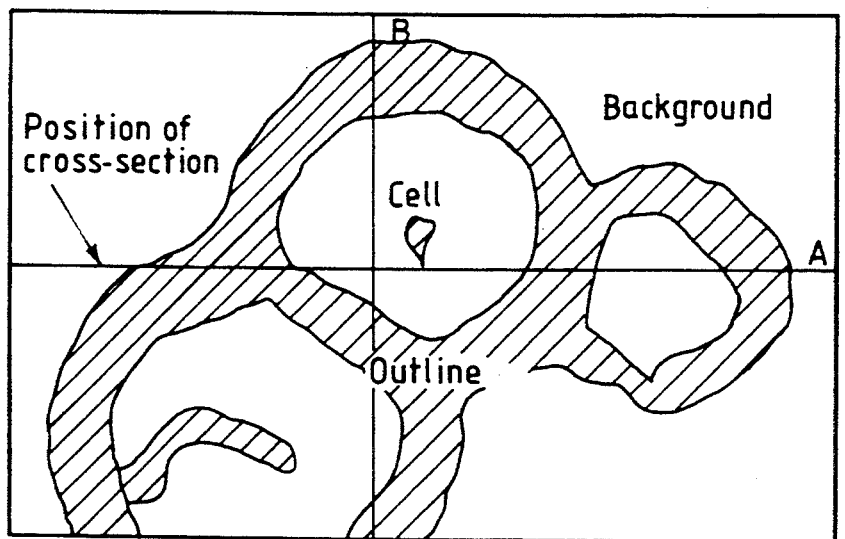
FIG. 10(a) illustrates the brightness in the vicinity of the cell in an original picture image.
Figure 10B:
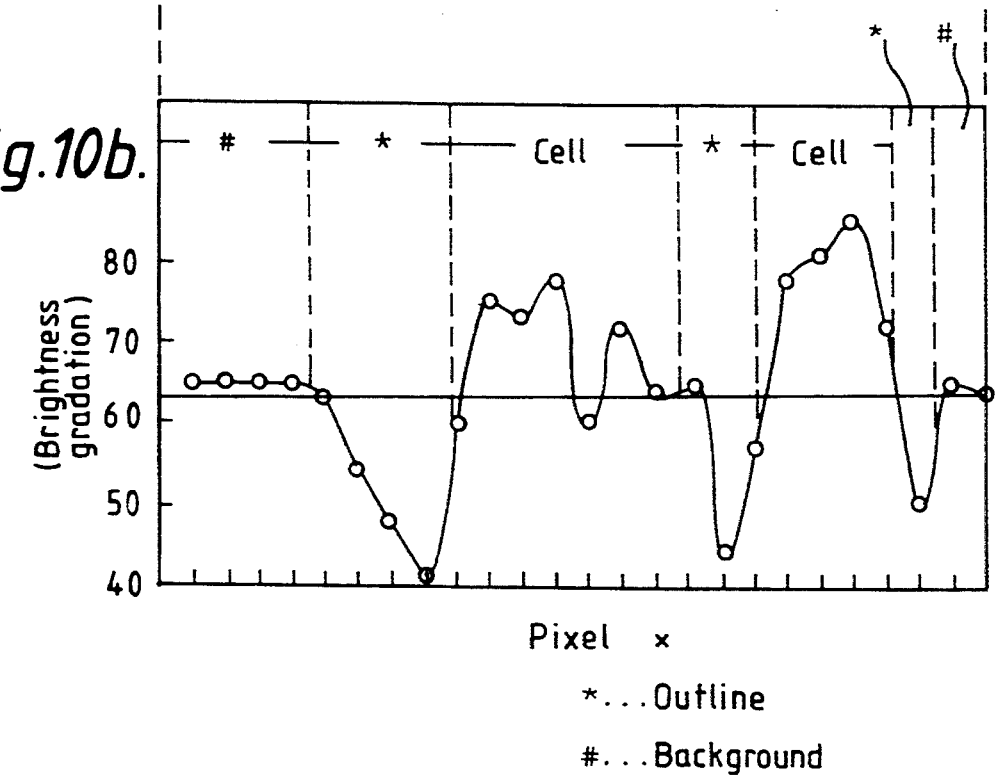
FIG. 10(b) is a graph showing the relationship between pixel position and brightness corresponding to brightness conditions.

FIG. 10(a) and 10(b) illustrate the brightness pattern shown at the boundary of one kind of cell in a picture image. The part corresponding to the outline shows a low brightness while the part corresponding the cell shows a high brightness. Between the outline and the cell there exists a large brightness difference. Such a feature also occurs for the microscopic spherical bodies. Therefore, both cells and microscopic spherical bodies can be recognized via the same sequence.

Figure 11:
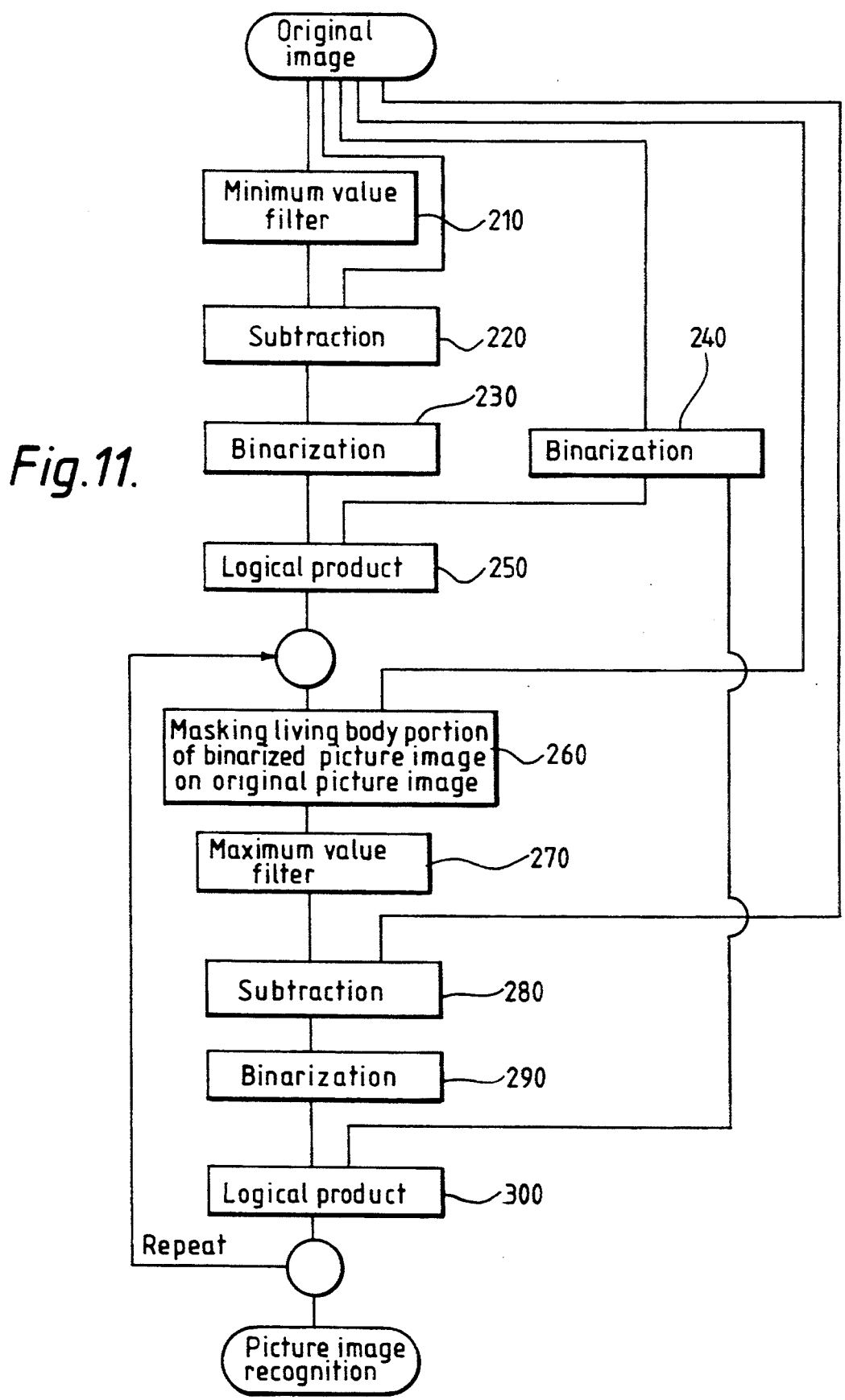
FIG. 11 is a flowchart showing a sequence for living body recognition by means of a recognition method making use of brightness differences.

FIG. 11 shows one example of a method corresponding to the step 120 in FIG. 9, making use of the brightness patterns discussed above to recognize cells and microscopic spherical bodies.

This recognition method is divided into a first stage in which a part of the living body is recognized and a second stage in which the recognised part is extended, to obtain the entire image of the cell.

In the step of recognizing a part of the cell, a minimum value filter is applied to the original picture image, and the original picture image is subtracted from that result (steps 210–220). These operations have, for two pixels located adjacent each other which have a large brightness difference therebetween, the effect of providing a brightness value of '1' for a pixel having a high brightness and '0' for a pixel having a low brightness value. When this operation is applied to the picture images generated by picking up the image of the culture liquid of animal cells, the pixels corresponding to the outlines of the cells and small particles with small areas have a low brightness. Thus, picture images of variable brightness are obtained in which the parts immediately inside the outlines show a high brightness. This picture image is fixed and binarized, and the parts with high brightness are selected. In this way, binarized picture images are obtained in which the number of pixels adjacent the outline are recognized from the pixel groups corresponding to the insides of cells (step 230).

There sometimes exists a large brightness difference between the pixels corresponding to the outline of the cells and those corresponding to the background of its outer circumference similar to the brightness difference between the cell and its outline, such that processing in the steps 210-230 are likely erroneously to recognize these differences as living bodies. However the brightness of these parts are normally low in comparison with the brightness level within the cells, so that these parts may be eliminated, with high reliability, by forming the logical product between the binarized picture images formed in step 230 and the binarized picture images obtained by directly binarizing the original picture images (step 240-250).

When the step of identifying a part of the living bodies has been completed, the areas of the respective living bodies which have been identified are small and the number of living bodies which have been identified is not exact because many parts of one living body may be identified. Therefore the identified part needs to be extended. This step makes use of the fact that the brightness of the inside of each cell is substantially constant.

Therefore, the living body portion identified in the previous step is masked onto the original picture images (step 260). The term 'masking' means that the brightness values of the pixels in variable density picture images having the same coordinates as pixels having a value of "1" in the binarized picture images are maintained unchanged and the brightness values of all the other pixels are made zero, to obtain variable brightness picture images. This processing operation causes the expansion starting point to be restricted to the part recognized in the prior step.

Subsequently, to this variable brightness picture image a maximum value filter is applied (step 270). This process generates, variable brightness picture images in which the brightness of the pixels corresponding to the parts recognized in the earlier steps and the parts adjacent thereto takes positive values and the brightness values of the other pixels, being background pixels, take the value '0'. When the original picture image is subtracted from this variable brightness picture image, a variable brightness picture image is obtained in which the background has a negative brightness, the outline has a high brightness and the inside of the body has a brightness about '0'(step 280). When this variable brightness picture image is binarized such that parts portions having a brightness between two threshold valves, for example between −5 and +15, are set to have a value "1", the parts corresponding to the insides of the living bodies are identified (step 290). The identified parts includes pixels which are located adjacent the living body prior to the expansion and have a small brightness difference from that part of the living body. Thus, expansion covering one pixel has been achieved.

The logical product with the original picture image is also generated (step 300). The purpose of the generator of the logical product is to prevent expansion from the part having recognized the living body toward the background beyond the outline.

The above recognition portion expansion step is repeated until no further expansion occurs. A standard number 1 of repetitions is 5 to 10. However even if the number of repetition is increased, there is no adverse effect on the identification of living bodies. Furthermore, the searching illustrated in FIG. 10 may be repeated in two mutually perpendicular directions A and B to increase accuracy. FIG. 10(*b*) then corresponds to direction A.

Figure 12:
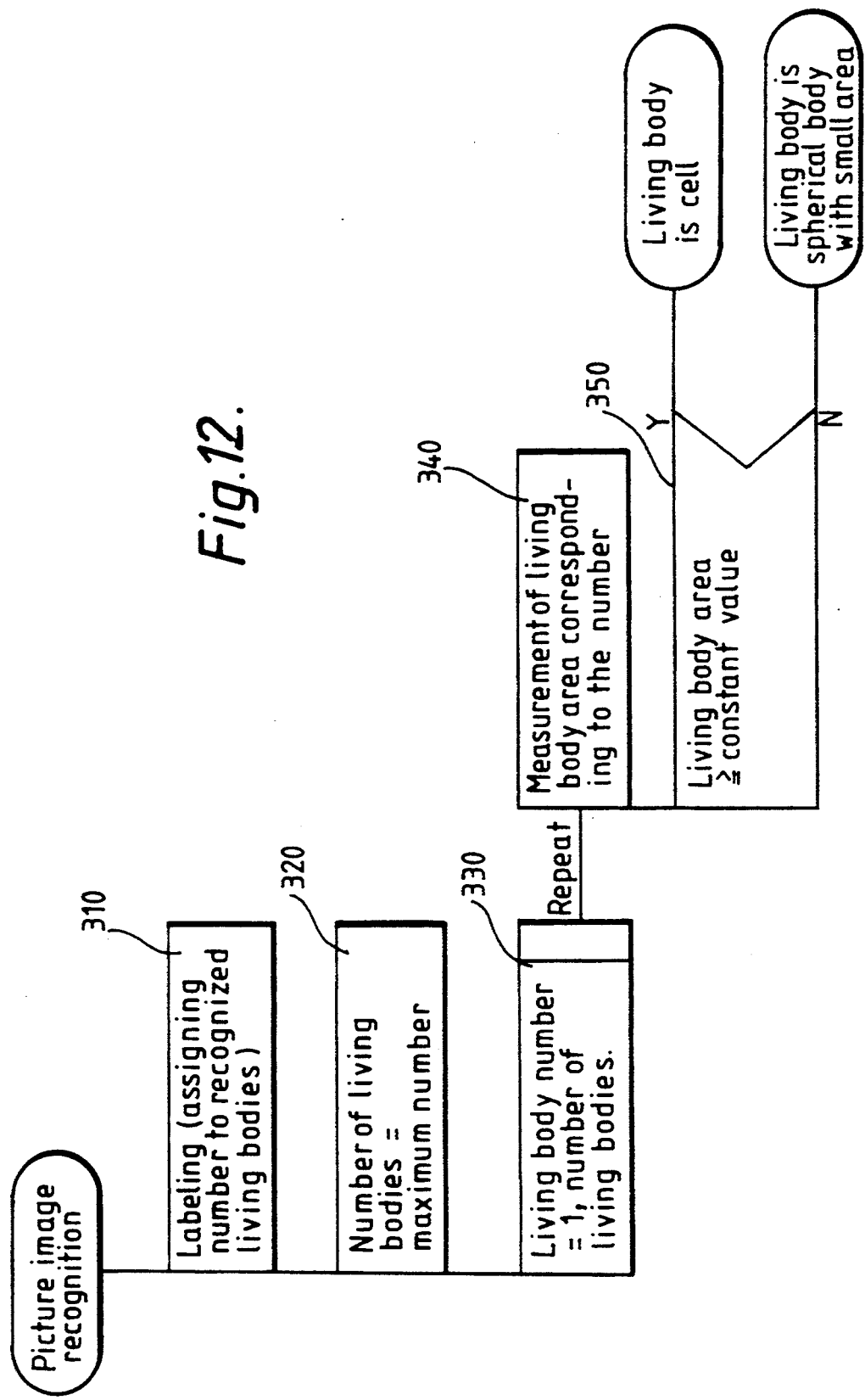
FIG. 12 is a flowchart showing an example of discrimination between cells and microscopic spherical bodies which are identified in the processing method of FIG. 9, based upon the areas of the bodies.

FIG. 12 shows an example of discrimination processing of cells and microscopic spherical bodies, both of which were identified in step 120 of FIG. 9 based upon the identified areas of these living bodies. This process is included in a part of step 130 in FIG. 9.

This discrimination method is carried out, after the area of each of the identified living bodies is measured, by determining whether the measured value is above a predetermined value. First, respective living bodies which are identified by the binary picture image are assigned respective numbers (labeling step 310). When the labeling is completed, the last number indicates the total number of living bodies. This value is substituted for the variable prepared for substituting the number of living bodies (step 320). Subsequently, in accordance with their number order discrimination is carried out, one by one, to determine whether the living body is a cell or a spherical body with a small area. Thus, the area of the living body with the corresponding number is measured (step 340). When the measured value is above a predetermined value, the living body is identified as a cell and when the measured value is below the predetermined value the living body is identified as a spherical body with a small area (step 350). This operation is repeated as many times as the number of living bodies (step 330).

Figure 13:
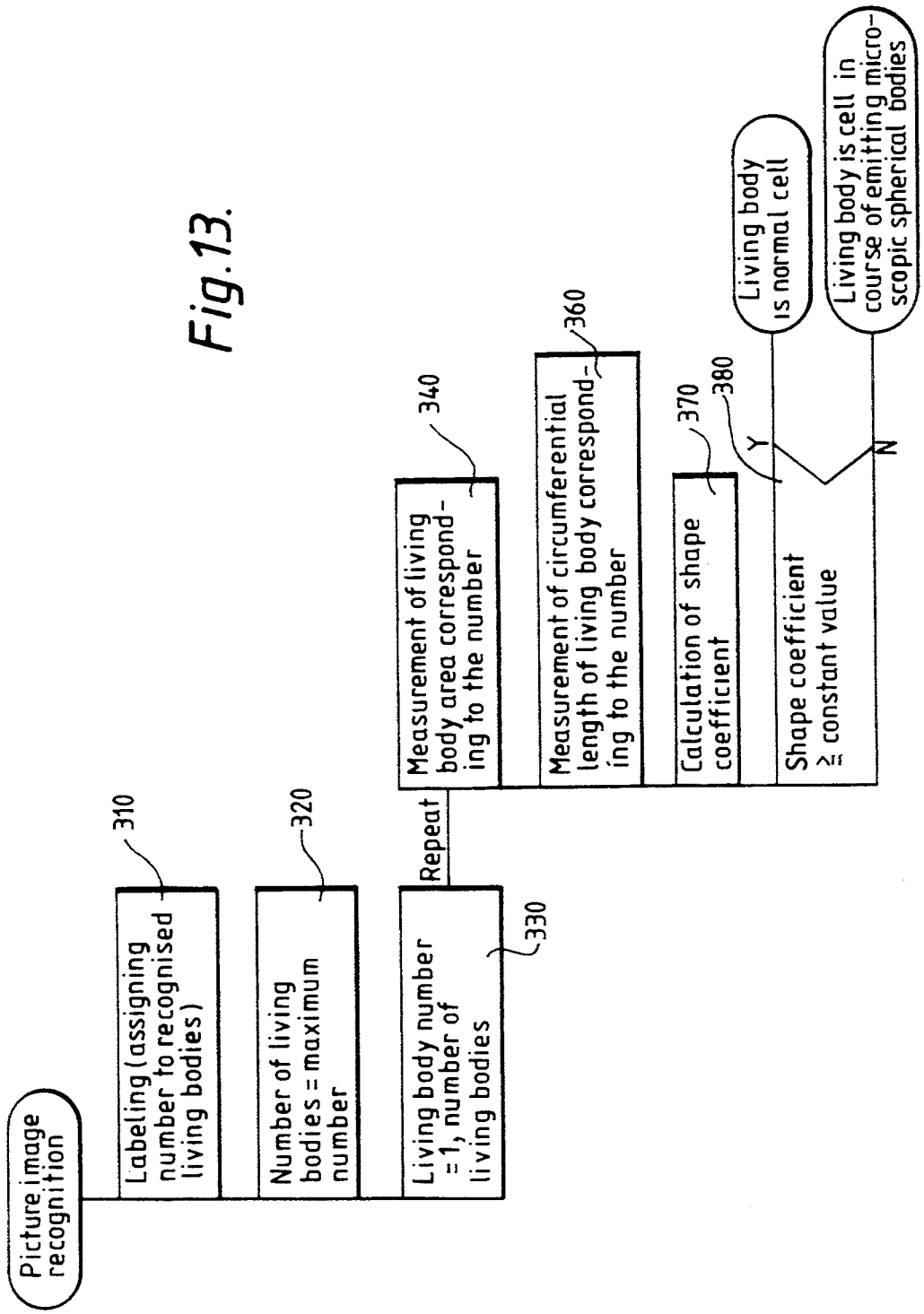
FIG. 13 is a flow chart showing an example of discrimination between ordinary cells and cells in the course of emitting microscopic spherical bodies, which cells are identified in the processing method of FIG. 9, based upon a shape coefficient.

FIG. 13 shows a method in which discrimination between the normal cells and the cells in the course of emitting microscopic spherical bodies, which have been recognized together, is performed. This method makes use of a coefficient called the shape coefficient. The shape coefficient is a coefficient which indicates the degree of roundness of the shape of the living body and is determined by comparing the actual area of the living body with the area of the living body obtained from its circumference length when the living body is assumed to be a circle. This is expressed by the following equation.

$$\frac{\text{actual area}}{(\text{circumferential length}/2)^2 \times \pi}$$

The coefficient calculated by comparing the actual circumference of the living body with the circumference of the living body obtained from its area when the living body is a complete circle, as indicated below, may also be used.

$$\frac{2\sqrt{\text{area} \times \pi}}{\text{actual circumferential length}}$$

When the call has many recesses and protrusions both values approach 0 and when the roundness of the cell is high, the values approach 1. When the shape coefficient is used for cell observation, and when a microscopic spherical body is in the course of being divided from a cell, the coefficient is small.

The method of FIG. 13 includes the following steps. First, respective living bodies which are identified in the binary picture image are assigned respective numbers (labeling step 310). When the labeling is completed, the last number indicates the total number of living bodies. This value is substituted for the variable prepared for substituting the number of living bodies (step 320). Subsequently, in accordance with their number order, discrimination is carried out, one by one, to determine whether the living body is a cell or a spherical body with a small area. Thus, the area of the living body (step 340) and the circumferential length (step 360) of the living body are measured, and the shape coefficient thereof are calculated by making use of either of the above equations for calculating the shape coefficient (step 370). Then, when the shape coefficient is above a predetermined value and near to 1, the body is identified as a normal cell and when the shape coefficient is below a predetermined value and near to 0 the body is identified as to be a cell in the course of emitting microscopic living body (step 380). These discrimination routines are repeated for each living body identified by numbers (step 330).

Figure 14:
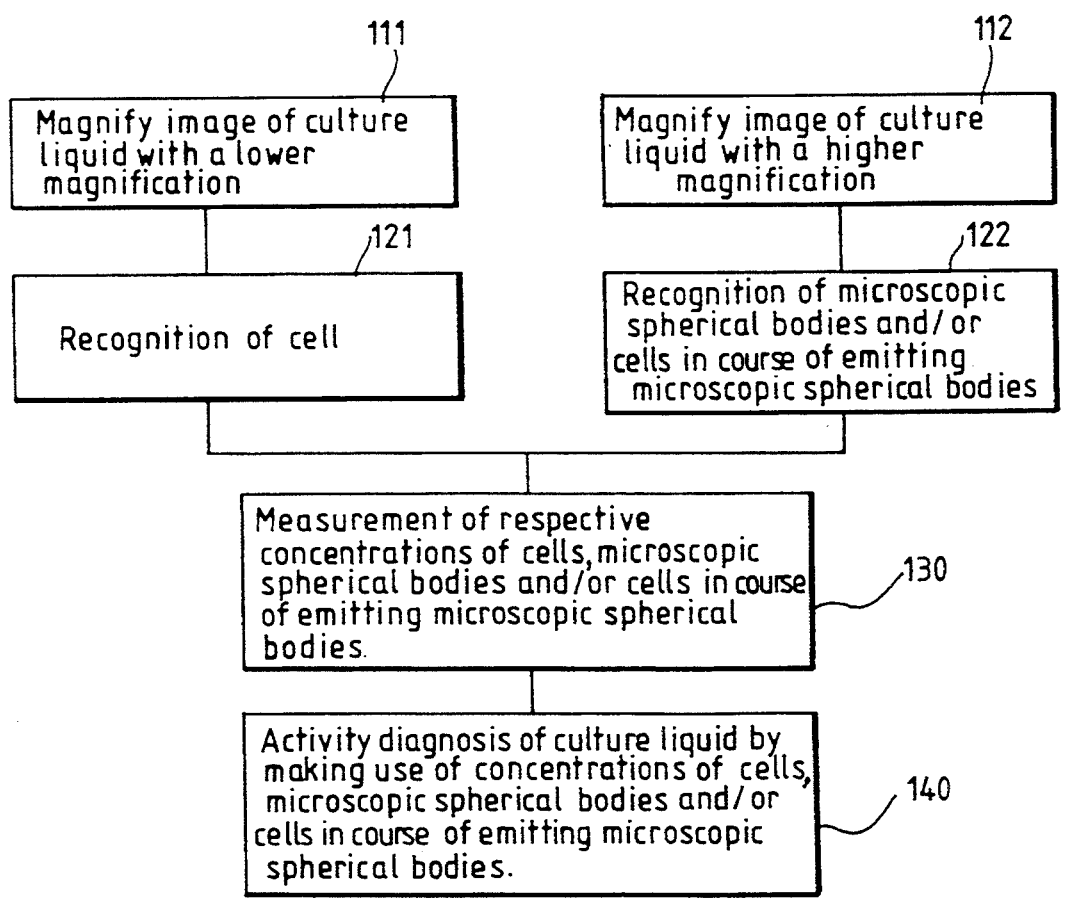
FIG. 14 is an example of processing when images of a culture liquid containing cells in suspension are identified at a plurality of different magnifications.

FIG. 14 shows an example of the operation when the image of a culture liquid containing cells in suspension is image picked-up with a plurality of different magnifications.

In step 111, the image of the culture liquid containing cells in suspension is picked-up with a relatively low magnification. The cells existing in the picture image are recognized at a step 112. Then, in a step 112, the image of the culture liquid which has been sampled simultaneously in the step 111 is picked-up with a comparatively high magnification, relative to that of the step 111. Either microscopic spherical bodies or cells in the course of emitting microscopic spherical bodies or the both may be identified from the picture image obtained in the step 112. In step 130, the concentrations of the cells and the microscopic spherical bodies are measured for every kind of living bodies, and in step 140 the activity of the culture liquid is diagnosed from the resultant concentrations.

Figure 15:
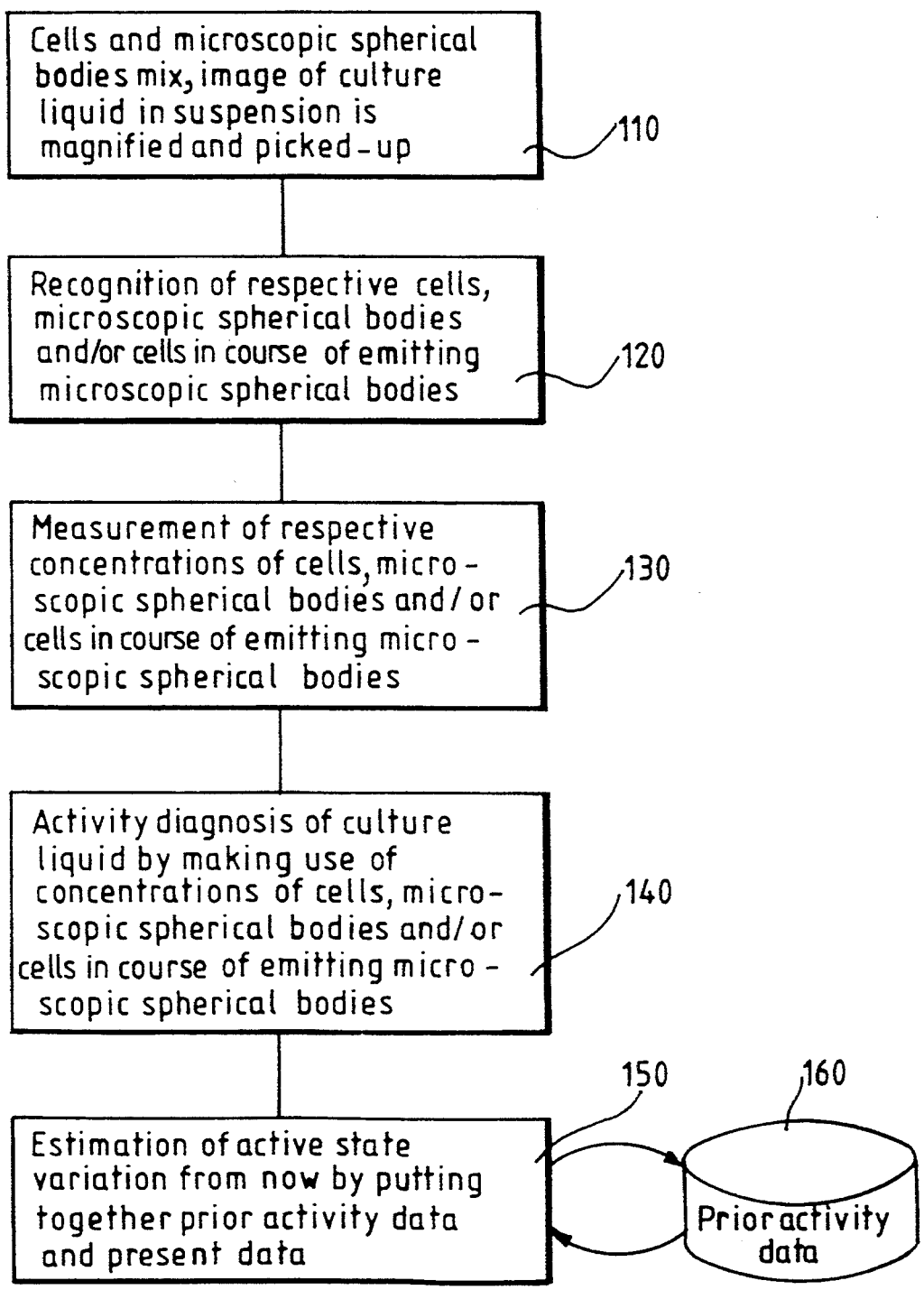
FIG. 15 is a flowchart showing an example of processing when a step, which estimates the variation of the current active state by exchange of data with means storing an earlier activity state, is included after the method shown in the flowchart of FIG. 9.
Figure 16:
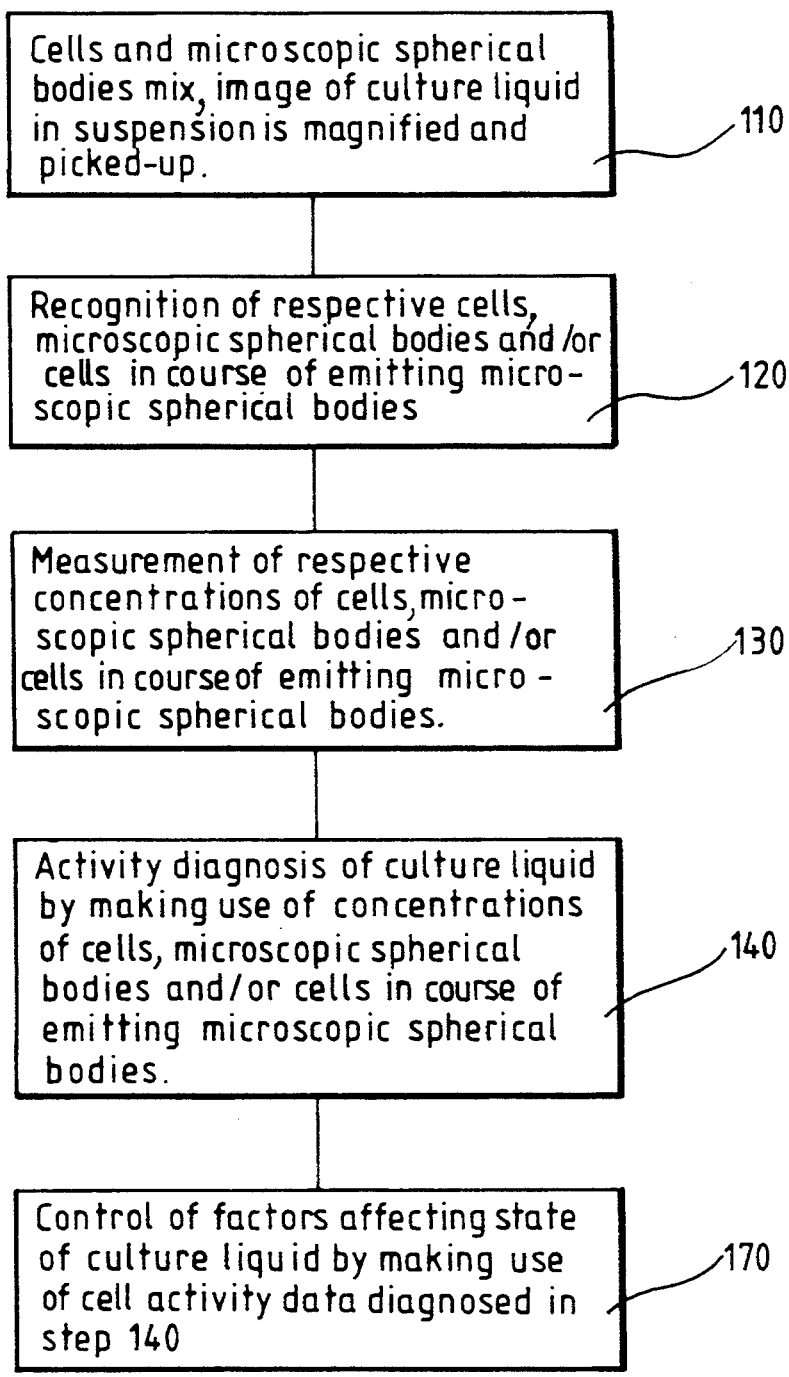
FIG. 16 to FIG. 18 are respectively flowcharts showing examples of processing when a processing step, which controls factors affecting the state of culture liquid based upon the obtained activity data, is added after the methods shown in the flowcharts of FIG. 9, FIG. 14 and FIG. 15, respectively.
Figure 17:
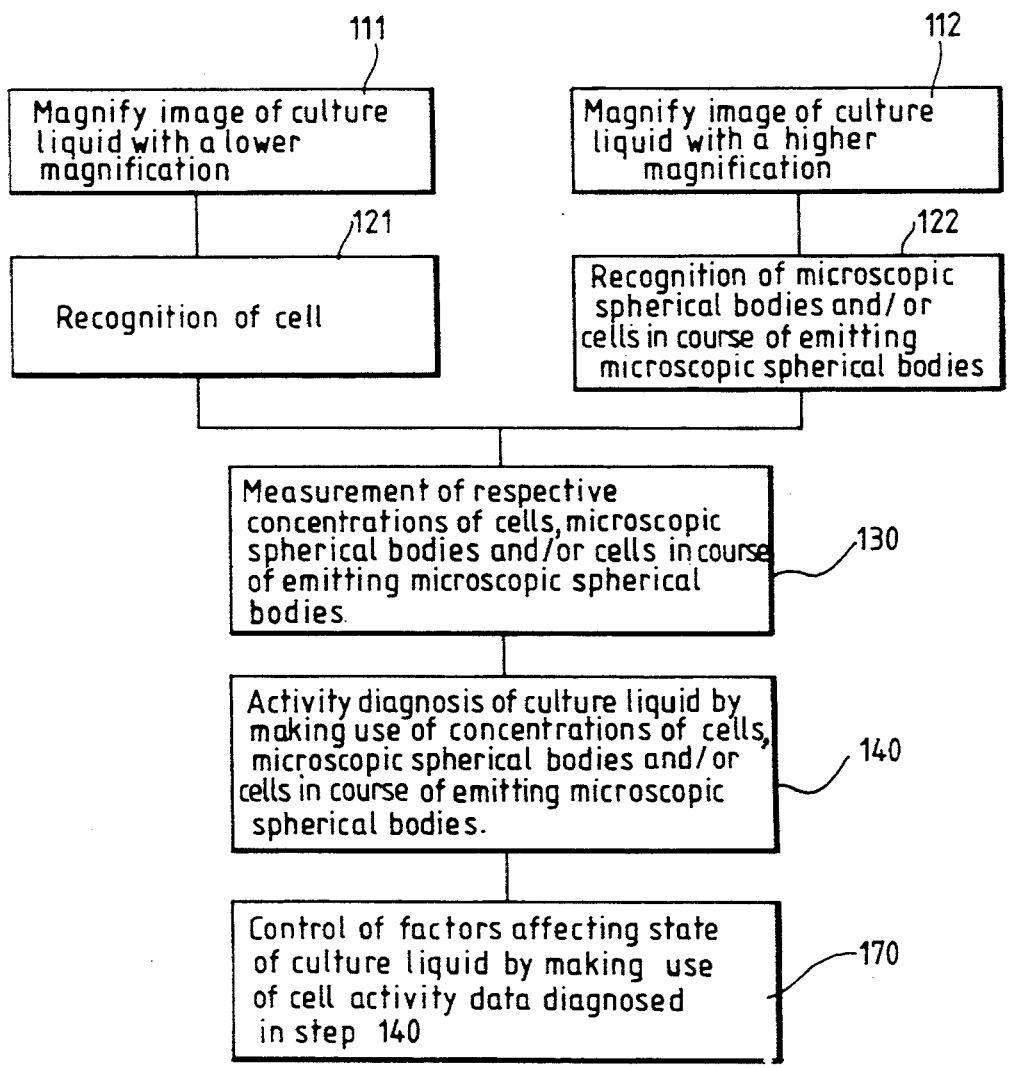
Figure 18:
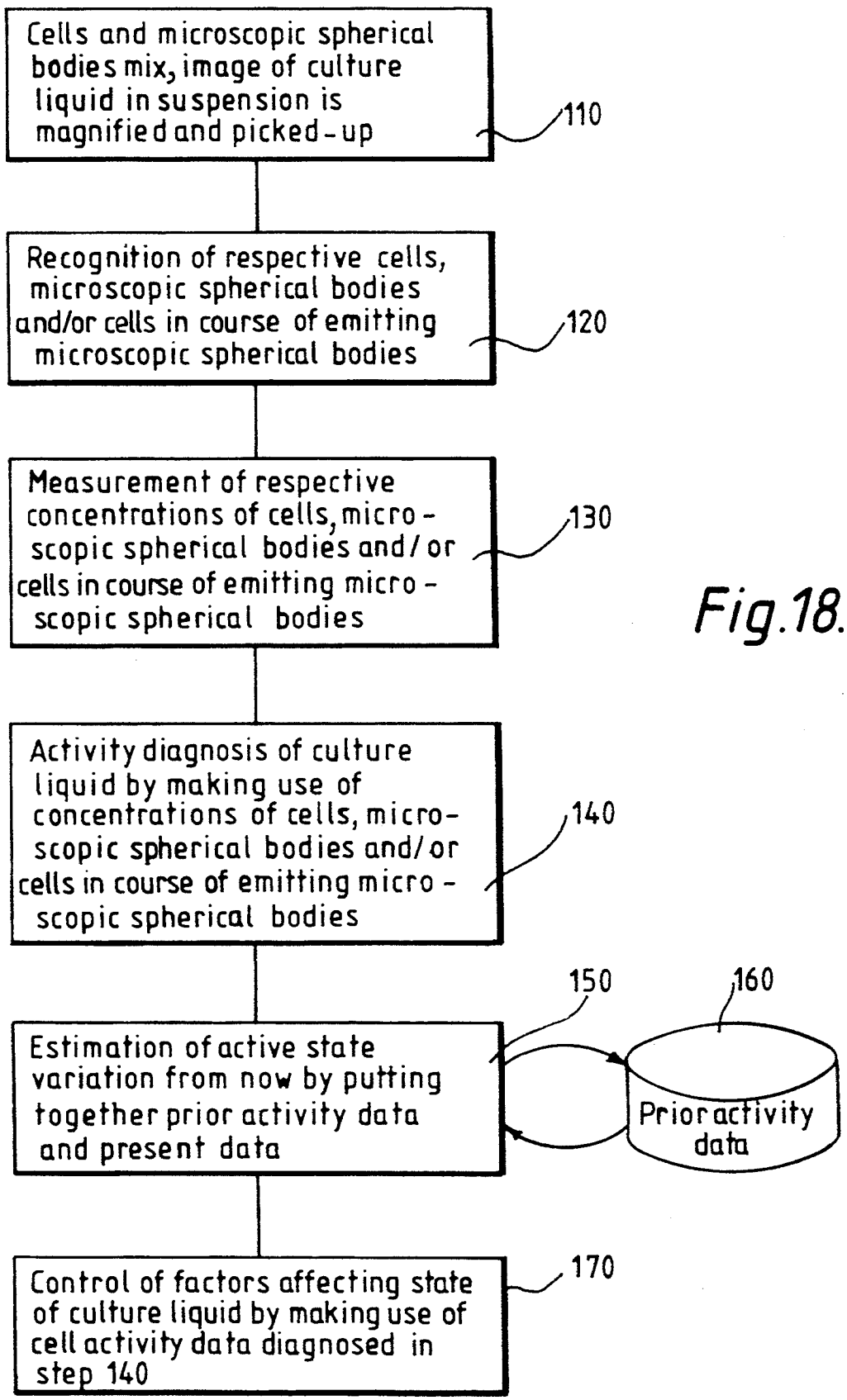

The present invention may provide a cell activity estimation and diagnosis method in which the cell activity data when the culture liquid was previously sampled is stored. Then, in the data read out from the storage means and the current activity data may be substituted into an equation such as a differential equation. The variation of the activity of the cells may then be estimated. In FIG. 15, the steps 110 to 140 are the same as those in FIG. 9. After these steps, a step 150 is carried out in which the variation of the activity of the cells is investigated by exchanging data with the storage means 160 which stores data representing previous activity. Another stage is then added subsequently, which controls factors affecting the culture liquid by making use of the resultant activity data. In FIG. 16 and FIG. 17, a step 170 is respectively shown, which controls factors affecting the state of the culture liquid by making use of the cell activity data obtained by the diagnosis result in step 140, after the same steps as in FIG. 9 and FIG. 14. Further, in FIG. 18, a step 170 is added, which controls factors affecting the state of the culture liquid by making use of both the activity diagnosis result from the step 140 and the estimation result in step 150, after the same steps as in FIG. 15.

Another embodiment of the present invention is illustrated in FIG. 19. In this embodiment, culture liquid is sampled from a cell culturing tank 470 and fed to an image pick-up device 420. The magnified picture images of the culture liquid image picked-up at an image pick-up device 420 are input to a picture image recognition device 430 which identifies cells and microscopic spherical bodies or cells in the course of emitting microscopic spherical bodies or both. A statistical processing device 440 discriminates the cells from the microscopic spherical bodies, determines the member thereof and determines the concentrations of both. A cell activity diagnosis device 50 calculates the activity of the cells in the culture liquid based upon the concentrations of these bodies and generates as output to e.g. a display and printer. A reference number 410 is a transparent container and a reference number 480 is a tank for sampled liquid after being subjected to the investigation. Unlike the embodiment shown in FIG. 6, automatic control of the cell culturing tank 470 does not occur. The control depends on the operator who determines the diagnosis results.

Another embodiment may be used which comprises a cell activity diagnosis device, which diagnosing cell activity in the culture liquid by comparing the current activity with prior data in a cell activity judging means.

Another embodiment will now be discussed with reference to FIG. 20. A timer generates driving signals which drive a pump of an image pick-up device 420. A culture liquid is sampled from a cell culture tank 470 and fed to an image pick-up device 420. Picture images are pick up a plurality of times with different magnifications and input to a picture image recognition device 430. The cells are recognized from picture images taken at one magnification and the microscopic spherical bodies or the cells in the course of emitting microscopic spherical bodies or both are recognized from picture images taken at another magnification. A picture image processing device 440 analyzes the living bodies (cells, microscopic spherical bodies and cells in the course of emitting microscopic spherical bodies) recognized by the picture image recognition device 430 and determines the respective concentrations. By using the ratios calculated from cells and either one of two kinds of other living bodies or the both as indexes, a cell activity diagnosis device 450 diagnoses the activity of cells in the cell culturing tank 10. The difference between this embodiment and that of FIG. 5 is that in this embodiment the culture condition is not controlled automatically but instead the information about cell activity is passed to the operator.

In the above embodiments, the type of cells is not specified. However, a preferred application of the present invention is for animal cell culturing. Some animal cells have the characteristic that the cells emit microscopic spherical bodies, which cannot be said to be cells, before the cells are dead. Hence, the cell activity diagnosis method and the cell culturing method explained hereinabove can be applied easily.

Figure 21:
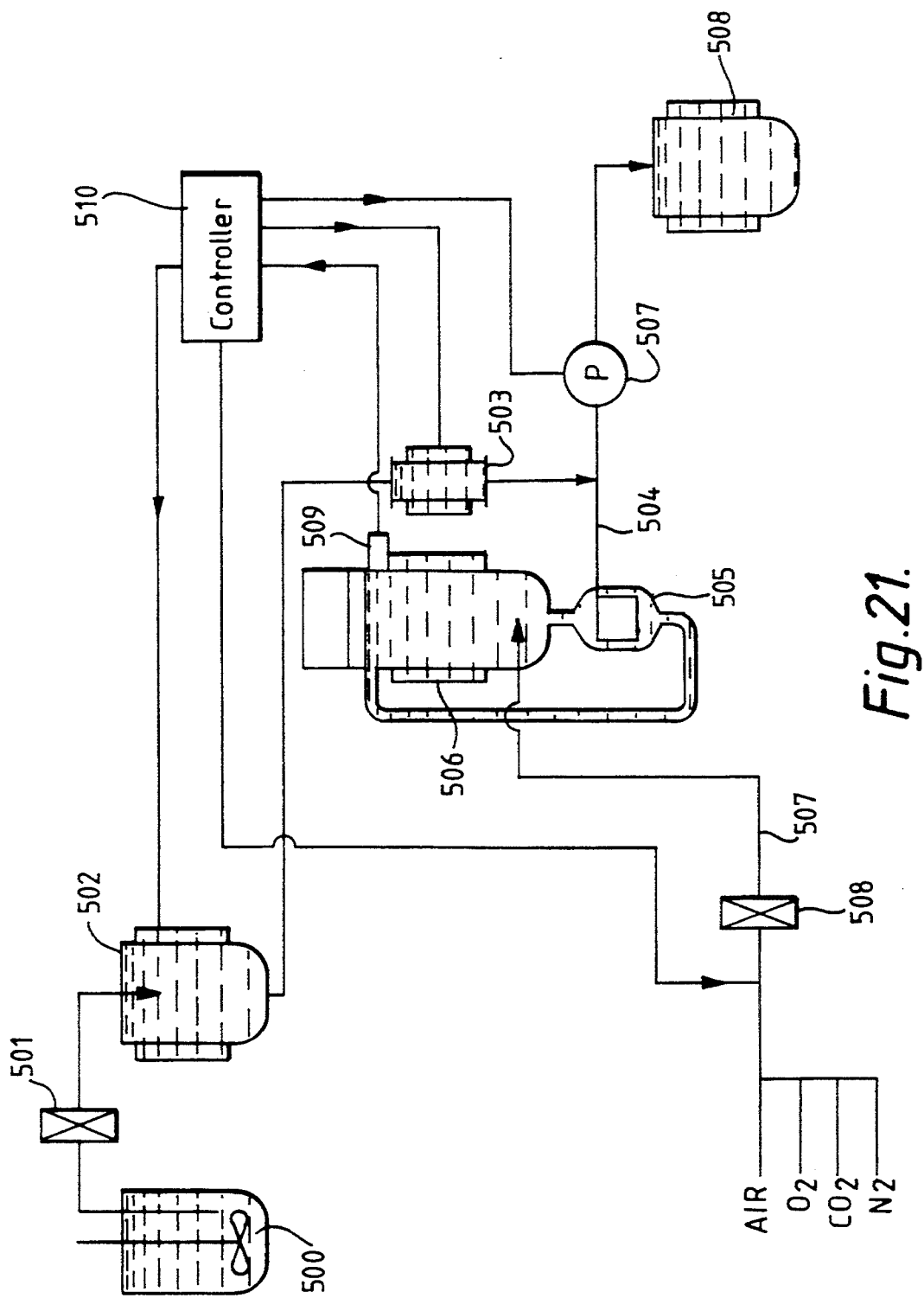
FIG. 21 is a schematic diagram of a practical cell culture system in which the present invention is embodied.

FIG. 21 is a schematic diagram of a practical cell culture system in which the present invention is embodied. Broth for the cell culture is mixed in a mixer 500 and passed via a filter 501 to a broth tank 502. Broth passes from the broth tank 502 via a temperature controller 503 to a duct 504, from which it may pass via a cell separator 505 to a culture vessel 506. A duct 507 containing a filter 508 may supply air, oxygen, carbon dioxide, and/or nitrogen to the culture vessel 506. By suitable operation of the flow of broth from the broth tank 502 via the temperature control 503 and cell separator 505 to the culture vessel 506, a suitable culture of microorganisms can be developed inside the culture vessel. At an appropriate time, a pump 507 is operated to withdraw broth from the culture vessel 506 via the cell separator 505 and the duct 504, and the separated broth is then passed to a collecting tank 508.

In accordance with the present invention, an image pick up device 509 monitors the cells, microscopic small particles, and cells in the course of emitting microscopic small particles, the image pick up device 509 operating in a manner corresponding to that described for the earlier embodiments. A controller 510 monitors the output of the image pick up device 509, to determine the viability of the culture in the cell vessel 506. The controller 510 may then control the conditions of the culture in the culture vessel by one or more of:

1. supplying additional broth from the broth tank 502 at a suitable temperature determined by the temperature controller 503;
2. supplying one or more of air, oxygen, carbon dioxide and nitrogen, via the duct 507;
3. removing broth from the culture vessel 506 by control of the pump 507, and passing that removed broth to the collecting tank 508.

Figure 22:
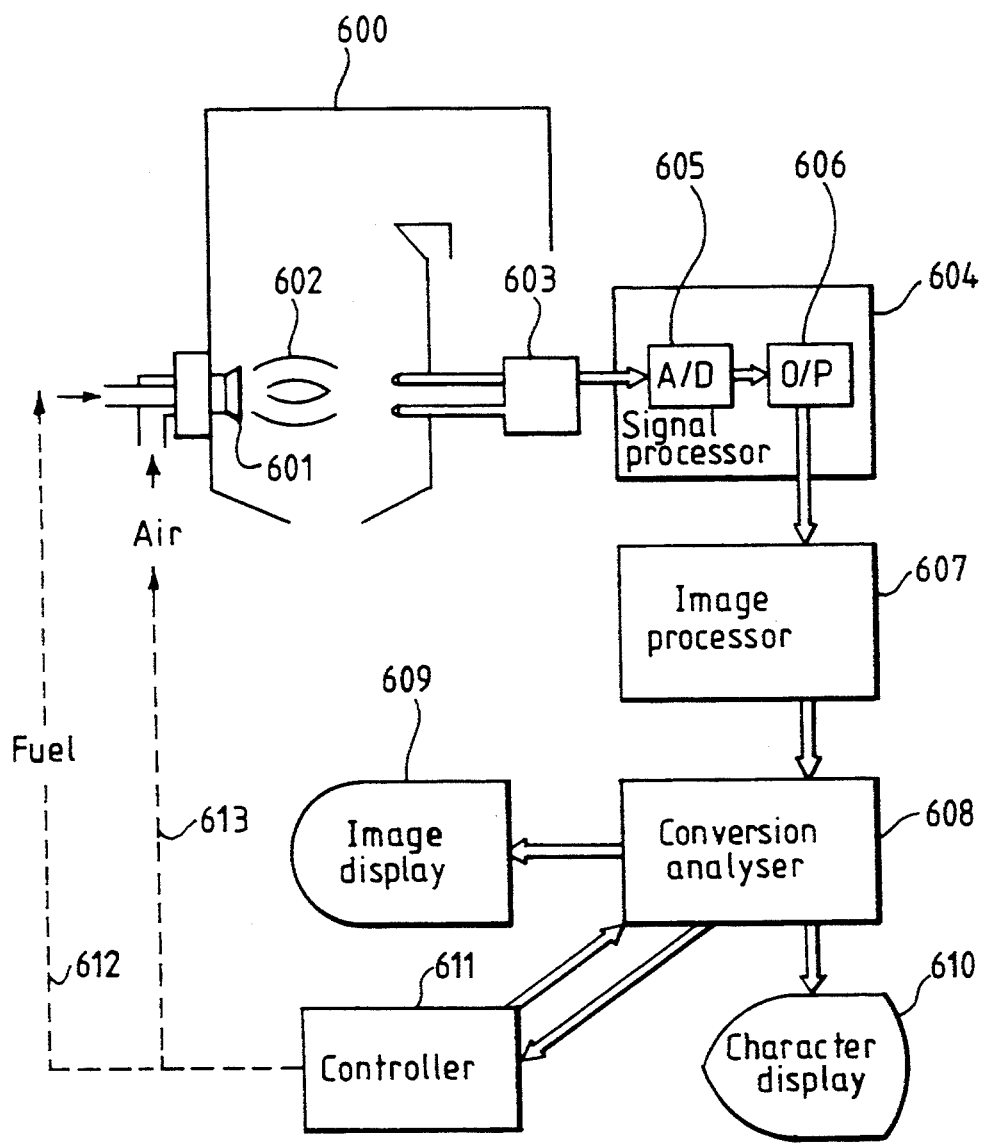
FIG. 22 is a schematic diagram of a flame investigation system according to the present invention.

In all the above embodiments, the present invention has been applied to the detection of a micro-organism in a culture thereof, but the present invention is not limited to the detection of microorganisms. FIG. 22 illustrates an embodiment in which the flame of a furnace is monitored. In the embodiment of FIG. 22, a furnace 600 has a nozzle 601 therein from which is generated a flame 602 for heating the furnace 600. An image pick up device 603 picks up the image of the flame 602 at two different magnifications, and passes respective signals to a signal processor 604 including an analog-to-digital converter 605 and an output unit 606 which outputs digital signals representing the images photographed by image pick up device 603 to an image processor 607. The image processor 607 processes the images and passes them to a conversion analyzer 608. Display 609 may show the image picked up by the image pick up device 603, whilst a character display 610 may display information relating to the results of the analysis of the images by the conversion analyzer 608. Thus, the operator may be presented both with a visual indication of the image itself, on image display 609, and information about the image on the character display 610.

In this way, it is possible to investigate two different properties of the flame 602, by picking up the image of the flame 602 using the image pick up device 603 at two different magnifications. Thus, at a low magnification, in which substantially the whole of the flame can be seen, the variation in brightness across the flame 602 can be investigated. At higher magnifications, a more detailed investigation of the temperature of part of the flame 602 can be obtained. A controller 611 may analyze the measurements carried out by the conversion analyzer 608, and then may control ducts 612 and 613 respectively supplying fuel and air to the nozzle 601. In this way, the flame 602 can be controlled by the controller 611 independence on the observed image. Thus, the generation of chemical species NOx and/or SOx may be observed and the fuel and air controlled accordingly.

Figure 23:
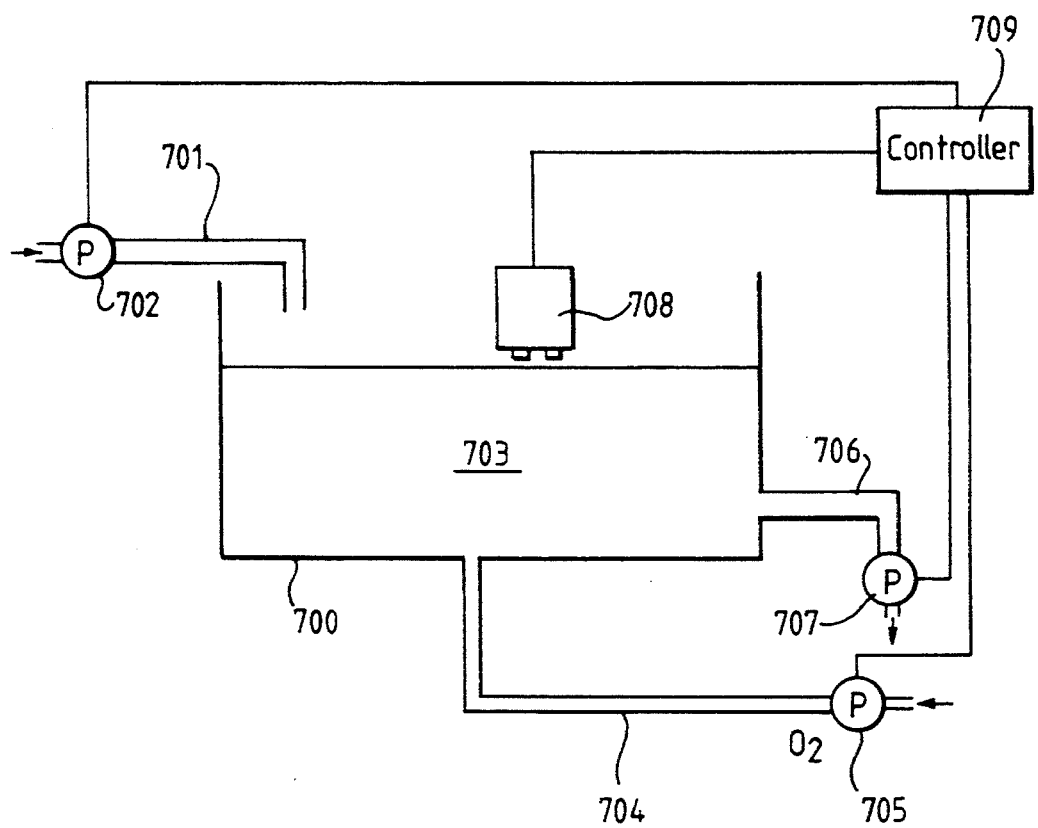
FIG. 23 is a schematic diagram of a sewage plant investigation system according to the present invention.

FIG. 23 shows the application of the present invention to a sewage plant based on activated sludge. The sewage plant has a main tank 700 which receives sewage via an inlet pipe 701, the supply of sludge being controlled by a pump 702. The activity of the sewage 703 in the tank 700 may be controlled by the supply of oxygen via a duct 704, controlled by a pump 705, and treated sewage may be removed from the tank 703 via an outlet 706 controlled by a pump 707.

In accordance with the present invention, an image pick up device 708 gets the image of the sewage 703 at two different magnifications, to enable different properties to be investigated. For example, at one magnification, the total density of microorganisms within the sewage 703 may be investigated, whilst at a higher magnification the density of a particular type of microorganisms may be investigated. A controller 709 receives signals from the image pick up device 708, and may then control the pumps 702, 705 and 707, accordingly to control the treatment of the sewage 703 in the tank 700.

Thus, the present invention permits objects which change with time to be investigated at two different magnifications, to enable characteristics of the object to be determined. On the basis of those characteristics, the conditions of the object may be varied, as desired.

What is claimed is:

1. A method of culturing micro-organisms, comprising:
   a) establishing a culture of said microorganisms;
   b) supplying culture material to said culture and removing culture material therefrom;
   c) repeatedly:
      (i) optically investigating first bodies of said micro-organisms of said culture at a first optical magnification, said optically investigating of said first bodies including picking up the image of said culture with an image pick-up device to obtain a first image and processing said first image, thereby to obtain the concentration of said first bodies in said culture;
      (ii) optically investigating second bodies of said micro-organisms of said culture at a second optical magnification, said optically investigating of said second bodies including picking up the image of said culture with an image pick-up device to obtain a second image and processing said second image, thereby to obtain the concentration of said second bodies in said culture;
   d) investigating the variation of concentration of said first and second bodies; and
   e) controlling said supplying and removing of said culture material on the basis of said variation of concentration of said first and second bodies.

2. A method according to claim 1, wherein said investigating of said variation of concentration includes deriving the ratio of said first and second bodies, and said controlling of said supplying and removing of said culture material is such as to maintain said ratio below a predetermined value of said ratio.

3. A method according to claim 2, wherein said predetermined value of said ratio is 2.

4. A method according to claim 1, wherein said optically investigating second bodies of said micro-organisms of said culture is effected independently of the result of said optically investigating first bodies of said micro-organisms of said culture.

5. A method of investigating a culture of micro-organisms, comprising:
   a) establishing said culture of said micro-organisms;
   b) repeatedly:
      (i) optically investigating first bodies of said micro-organisms of said culture at a first optical magnification, said optically investigating of said first bodies including picking up the image of said culture with an image pick-up device to obtain a first image and processing said first image, thereby to obtain the concentration of said first bodies in said culture;
   c) (ii) optically investigating second bodies of said micro-organisms of said culture at a second optical magnification, said optically investigating of said second bodies including picking up the image of said culture with an image pick-up device to obtain a second image and processing said second image, thereby to obtain the concentration of said second bodies in said culture;
   d) repeatedly storing data representing said concentration of said first and second bodies;
   e) comparing said data for a plurality of investigations of said first and second properties; and
   f) controlling said culture on a basis of a comparison result obtained in step e).

6. An apparatus for controlling a culture of micro-organisms, comprising:
   a container means for containing said culture of said micro-organisms;
   a feed means for supplying and removing culture material from said container means;
   an investigation means for repeatedly investigating said culture optically, said investigation means including at least one image pick-up device for picking up the image of said culture at first and second magnifications to derive first and second images;
   a processing means for processing said first and second images to derive concentrations of first and second bodies of said micro-organisms in said culture;
   an analysis means for comparing the concentrations of said first and second bodies derived by said repeated investigating by said investigation means, to derive an analysis result; and
   a control means for controlling said feed means on the basis of said analysis result.

* * * * *